(12) United States Patent
Powell et al.

(10) Patent No.: US 8,435,523 B2
(45) Date of Patent: May 7, 2013

(54) ANTIBODIES AGAINST NERVE GROWTH FACTOR (NGF) WITH ENHANCED IN VIVO STABILITY

(75) Inventors: John Powell, Cambridgeshire (GB); Duncan Casson, Royston (GB); Mark Maginn, Wilburton (GB); Wei Liu, Mundelein (IL); Sandeep Dutta, Gurnee (IL); Andrea Best, Lake Forest (IL); Jerry A. Hall, Gurnee (IL)

(73) Assignee: Abbott Research B.V., Zwolle (NL)

(*) Notice: Subject to any disclaimer, the term of this patent is extended or adjusted under 35 U.S.C. 154(b) by 438 days.

(21) Appl. No.: 12/773,488

(22) Filed: May 4, 2010

(65) Prior Publication Data

US 2010/0278839 A1  Nov. 4, 2010

Related U.S. Application Data

(60) Provisional application No. 61/175,228, filed on May 4, 2009, provisional application No. 61/227,251, filed on Jul. 21, 2009, provisional application No. 61/238,813, filed on Sep. 1, 2009, provisional application No. 61/252,314, filed on Oct. 16, 2009.

(51) Int. Cl.
*A61K 39/395* (2006.01)
*C07K 16/22* (2006.01)

(52) U.S. Cl.
USPC .................. 424/145.1; 514/17.7; 530/388.24

(58) Field of Classification Search ............... None
See application file for complete search history.

(56) References Cited

U.S. PATENT DOCUMENTS

| | | | |
|---|---|---|---|
| 4,230,691 A | 10/1980 | Young | |
| 6,017,878 A | 1/2000 | Saragovi et al. | |
| 6,919,426 B2 | 7/2005 | Boone et al. | |
| 7,252,822 B2 | 8/2007 | Shelton et al. | |
| 7,255,860 B2 | 8/2007 | Shelton et al. | |
| 7,371,559 B2 | 5/2008 | Boone et al. | |
| 7,425,329 B2 | 9/2008 | Shelton et al. | |
| 7,449,616 B2 | 11/2008 | Pons et al. | |
| 7,569,364 B2 | 8/2009 | Rosenthal et al. | |
| 7,601,818 B2 | 10/2009 | Wild, Jr. et al. | |
| 7,655,231 B2 | 2/2010 | Shelton et al. | |
| 7,655,232 B2 | 2/2010 | Pons et al. | |
| 7,727,527 B2 | 6/2010 | Shelton | |
| 7,795,413 B2 | 9/2010 | Wild, Jr. et al. | |
| 7,988,967 B2 | 8/2011 | MacDonald et al. | |
| 8,007,800 B2 | 8/2011 | Shelton et al. | |
| 2001/0046959 A1 | 11/2001 | Buchkovich et al. | |
| 2004/0071701 A1 | 4/2004 | Delafoy et al. | |
| 2004/0131615 A1 | 7/2004 | Shelton et al. | |
| 2004/0228862 A1 | 11/2004 | Shelton et al. | |
| 2004/0237124 A1 | 11/2004 | Pons et al. | |
| 2005/0074821 A1 | 4/2005 | Wild et al. | |
| 2006/0147450 A1 | 7/2006 | Shelton | |
| 2007/0264195 A1 | 11/2007 | Nykiaer et al. | |
| 2008/0033157 A1 | 2/2008 | Wild et al. | |
| 2008/0063635 A1 | 3/2008 | Takahashi et al. | |
| 2008/0081040 A1 | 4/2008 | Shelton et al. | |
| 2008/0107658 A1 | 5/2008 | Franks et al. | |
| 2008/0182978 A1 | 7/2008 | Rosenthal et al. | |
| 2008/0213282 A1 | 9/2008 | Jacob et al. | |
| 2009/0041717 A1 | 2/2009 | MacDonald et al. | |
| 2009/0155274 A1 | 6/2009 | Wild, Jr. et al. | |
| 2009/0208490 A1 | 8/2009 | Pavone et al. | |
| 2009/0300780 A1 | 12/2009 | Cattaneo et al. | |
| 2010/0034818 A1 | 2/2010 | Wild, Jr. et al. | |
| 2010/0055097 A1 | 3/2010 | Kaisheva et al. | |
| 2010/0111970 A1 | 5/2010 | Pons et al. | |
| 2010/0143355 A1 | 6/2010 | Shelton et al. | |
| 2010/0240582 A1 | 9/2010 | Boone et al. | |
| 2010/0260775 A1 | 10/2010 | Mills et al. | |
| 2010/0267934 A1 | 10/2010 | Van De Winkel et al. | |
| 2011/0014208 A1 | 1/2011 | Macdonald et al. | |
| 2011/0033447 A1 | 2/2011 | Rosenthal et al. | |
| 2011/0091476 A1 | 4/2011 | Wild, Jr. et al. | |
| 2011/0104164 A1 | 5/2011 | Cattaneo et al. | |
| 2011/0105728 A1 | 5/2011 | Cattaneo et al. | |
| 2011/0191872 A1 | 8/2011 | Cattaneo et al. | |
| 2011/0243961 A1 | 10/2011 | Shelton et al. | |
| 2011/0256587 A1 | 10/2011 | Macdonald et al. | |

FOREIGN PATENT DOCUMENTS

| | | |
|---|---|---|
| EP | 0578515 | 1/1994 |
| EP | 0592106 | 4/1994 |
| EP | 1891966 | 2/2008 |
| EP | 2100902 | 9/2009 |
| EP | 2191846 | 6/2010 |

(Continued)

OTHER PUBLICATIONS

Berardi et al., "Monoclonal antibodies to nerve growth factor affect the postnatal development of the visual system," Proc. Natl. Acad. Sci. USA, 91:684-688 (1994).
Boss et al., Immunol. Today, 6:12-13 (1985).
Bothwell, "p75NTR: a receptor after all," Science, 272(5261):506-507 (1996).
Cattaneo et al., "Functional Blockade of Tyrosine Kinase a in the Rat Basal Forebrain in a Novel Antagonistic Anti Receptor Monoclonal Antibody," J. Neurosci., 19(22):9687-9697 (1999).
Graziano et al., "Construction and characterization of a humanized anti-gamma-Ig receptor type I (Fc gamma RI) monoclonal antibody," J. Immunol., 155(10):4996-5002 (1995).
Harding et al., "Class switching in human immunoglobulin transgenic mice," Ann. NY Acad. Sci., 764:536-546 (1995).
Hinton et al., "An engineered human IgG1 antibody with longer serum half-life," J. Immunol., 176(1):346-356 (2006).
Hinton et al., "Engineered human IgG antibodies with longer serum half-lives in primates," J. Biol.. Chem., 279 (8):6213-6216 (2004).
Morrison, "Transfectomas provide novel chimeric antibodies," Science, 229(4719):1202-1207 (1985).

(Continued)

*Primary Examiner* — Robert C Hayes
(74) *Attorney, Agent, or Firm* — McAndrews, Held & Malloy, Ltd.

(57) ABSTRACT

The present invention provides anti-nerve growth factor (NGF) antibodies that contain an IgG4 constant region comprising a stabilizing hinge region mutation and wherein the antibodies exhibit an unexpectedly long serum half life in cynomolgus monkeys. Pharmaceutical compositions comprising the anti-NGF antibodies, nucleic acids encoding the NGF antibodies, host cells for expressing the NGF antibodies and methods of using the antibodies for treating NGF-related diseases or conditions are also provided.

9 Claims, 7 Drawing Sheets

FOREIGN PATENT DOCUMENTS

| | | |
|---|---|---|
| EP | 2206728 | 7/2010 |
| EP | 2263692 | 12/2010 |
| EP | 2270048 | 1/2011 |
| WO | 92/09631 | 6/1992 |
| WO | 90/10644 | 9/1999 |
| WO | 00/73344 | 12/2000 |
| WO | 01/10203 | 2/2001 |
| WO | 01/64247 | 9/2001 |
| WO | 01/78698 | 10/2001 |
| WO | 02/096458 | 12/2002 |
| WO | 2004/026329 | 4/2004 |
| WO | 2004/032852 | 4/2004 |
| WO | 2004/032870 | 4/2004 |
| WO | 2004/056385 | 7/2004 |
| WO | 2004/058184 | 7/2004 |
| WO | 2004/065560 | 8/2004 |
| WO | 2004/073653 | 9/2004 |
| WO | 2005/000194 | 1/2005 |
| WO | 2005/019266 | 3/2005 |
| WO | 2005/044293 | 5/2005 |
| WO | 2005/061540 | 7/2005 |
| WO | 2005/061540 A2 * | 7/2005 |
| WO | 2005/105847 | 11/2005 |
| WO | 2005/111077 | 11/2005 |
| WO | 2006/077441 | 7/2006 |
| WO | 2006/110883 | 10/2006 |
| WO | 2006/131951 | 12/2006 |
| WO | 2006/131952 | 12/2006 |
| WO | 2006/137106 | 12/2006 |
| WO | 2008/145142 | 12/2008 |
| WO | 2009/023540 | 2/2009 |
| WO | 2009/077993 | 6/2009 |
| WO | 2010/128398 | 11/2010 |
| WO | 2011/116090 | 9/2011 |

OTHER PUBLICATIONS

Myers et al., "Optimal alignments in linear space," Comput. Appl. Biosci., 4(1):11-17 (1988).

Needleman et al., "A general method applicable to the search for similarities in the amino acid sequence of two proteins," J. Mol. Biol., 48(3):443-453 (1970).

Petkova et al., "Enhanced half-life of genetically engineered human IgG1 antibodies in a humanized FcRn mouse model: potential application in humorally mediated autoimmune disease," Itn. Immunol., 18(12):1759-1769 (2006).

Ro et al., "Effect of NGF and anti-NGF on neuropathic pain in rats following chronic constriction injury of the sciatic nerve," Pain, 79:265-274 (1999).

Ruberti et al., "Phenotypic knockout of nerve growth factor in adult transgenic mice reveals severe deficits in basal forebrain cholinergic neurons, cell death in the spleen, and skeletal muscle dystrophy," J. Neurosci., 20(7):2589-2601 (2000).

Ruberti et al., "The use of the RACE method to clone hybridoma cDNA when V region primers fail," J. Immunol. Methods, 173:33-39 (1994).

Rudikoff et al., "Single amino acid substitution altering antigen-binding specificity," Proc. Natl. Acad. Sci. Usa, 79 (6):1979-1983 (1982).

Saragovi et al., "Development of pharmacological agents for targeting neurotrophins and their receptors," Trends Pharmacol. Sci., 21(3):93-98 (2000).

Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276 (9):6591-6604 (2001).

Stephens et al., "Comprehensive pharmacokinetics of a humanized antibody and analysis of residual anti-idiotypic responses," Immunology, 85(4):668-674 (1995).

Tripathy et al., "TrkA kinase inhibitors from a library of modified and isosteric Staurosporine aglycone," Bioorg. Med. Chem. Lett., 18(12):3551-3555 (2008).

Angal et al., "A Single Amino Acid Substitution Abolishes the Heterogeneity of Chimeric Mouse/Human (IgG4) Antibody," Mol. Immunol., 30(1)105-108 (1993).

Cattaneo et al., "Three Distinct Types of Monoclonal Antibodies After Long-Term Immunization of Rats with Mouse Nerve Growth Factor," J. Neurochem., 50:1003-1010 (1988).

Correia, "Stability of IgG isotypes in serum," mAbs, 2(3):1-12 (2010).

International Preliminary Report on Patentability in PCT/IB2010/001210 dated Nov. 9, 2011.

International Search Report in PCT/IB2010/001210 dated Sep. 10, 2010.

Ruberti et al., "Cloning and Expression of an Anti-Nerve Growth Factor (NGF) Antibody for Studies Using the Neuroantibody Approach," Cell. Mol. Neurobiol., 13(5):559-568 (1993).

* cited by examiner

ANTIBODIES AGAINST NERVE GROWTH FACTOR (NGF) WITH ENHANCED IN VIVO STABILITY

CROSS REFERENCE SECTION

The subject application claims priority to pending U.S. Provisional Patent Application Ser. No. 61/175,228 filed on May 4, 2009, and pending U.S. Provisional Application Ser. No. 61/227,251 filed on Jul. 21, 2009, and pending U.S. Provisional Application Ser. No. 61/238,813 filed on Sep. 1, 2009, and pending U.S. Provisional Application Ser. No. 61/252,314 filed on Oct. 16, 2009, all of which are hereby incorporated in their entirety by reference.

BACKGROUND OF THE INVENTION

Nerve growth factor (NGF) is a secreted protein that was discovered over 50 years ago as a molecule that promotes the survival and differentiation of sensory and sympathetic neurons. The beta chain of NGF is solely responsible for the nerve growth stimulating activity of NGF. The beta chain homodimerizes and is incorporated into a larger protein complex. NGF is a member of a family of neurotrophic factors known as neurotrophins NGF binds with high affinity to a tropomyosin receptor kinase known as TrkA. NGF is also capable of binding a receptor known as $p75^{NTR}$, a member of the tumor necrosis factor receptor superfamily, which also interacts with other neurotrophins The structure and function of NGF is reviewed in, for example, Sofroniew, M. V. et al. (2001) *Annu. Rev. Neurosci.* 24:1217-1281; Weismann, C. and de Vos, A. M. (2001) *Cell. Mol. Life. Sci.* 58:748-759; Fahnestock, M. (1991) *Curr. Top. Microbiol. Immunol.* 165: 1-26.

Although NGF was originally identified for its ability to promote the survival and differentiation of neurons, there is growing evidence that these developmental effects are only one aspect of the biology of NGF. In particular, NGF has been implicated in the transmission and maintenance of persistent or chronic pain. For example, both local and systemic administration of NGF have been shown to elicit hyperalgesia and allodynia (Lewin, G. R. et al. (1994) *Eur. J. Neurosci.* 6:1903-1912). Intravenous infusion of NGF in humans produces a whole body myalgia while local administration evokes injection site hyperalgesia and allodynia in addition to the systemic effects (Apfel, S. C. et al. (1998) *Neurology* 51:695-702). Furthermore, in certain forms of cancer, excess NGF facilitates the growth and infiltration of nerve fibers with induction of cancer pain (Zhu, Z. et al. (1999) *J. Clin. Oncol.* 17:241-228).

The involvement of NGF in chronic pain has led to considerable interest in therapeutic approaches based on inhibiting the effects of NGF (see e.g., Saragovi, H. U. and Gehring, K. (2000) *Trends Pharmacol. Sci.* 21:93-98). For example, a soluble form of the TrkA receptor was used to block the activity of NGF, which was shown to significantly reduce the formation of neuromas, responsible for neuropathic pain, without damaging the cell bodies of the lesioned neurons (Kryger, G. S. et al. (2001) *J. Hand Surg.* (Am.) 26:635-644).

Another approach to neutralizing NGF activity is the use of anti-NGF antibodies, examples of which antibodies have been described (see e.g., PCT Publication Nos. WO 2001/78698, WO 2001/64247, WO 2002/096458, WO 2004/032870, WO 2005/061540, WO 2006/131951, WO 2006/110883, U.S. Pat. No. 7,449,616; U.S. Publication Nos. US 20050074821, US 20080033157, US 20080182978 and US 20090041717). In animal models of neuropathic pain (e.g., nerve trunk or spinal nerve ligation) systemic injection of neutralizing antibodies to NGF prevents both allodynia and hyperalgesia (Ramer, M. S, and Bisby, M. A. (1999) *Eur. J. Neurosci.* 11:837-846; Ro, L. S. et al. (1999) *Pain* 79:265-274). Furthermore, treatment with a neutralizing anti-NGF antibody produces significant pain reduction in a murine cancer pain model (Sevcik, M. A. et al. (2005) *Pain* 115:128-141).

Thus, in view of the foregoing, additional NGF antagonists are desirable.

SUMMARY OF THE INVENTION

This invention provides anti-NGF antibodies that exhibit enhanced in vivo stability. In particular, the invention provides an anti-NGF antibody comprising a human IgG4 constant region, wherein the human IgG4 constant region comprises a mutation, preferably a hinge region mutation, and wherein the antibody exhibits an unexpectedly long terminal elimination half life, such as a terminal elimination half life in a cynomolgus monkey of at least 15 days and typically in the range of about 15 to about 22 days (or a range of 15 days to 22 days), or in a range of about 15 days to 28 days (or in a range of 15 days to 28 days), or in the range of about 21 days to about 28 days (or in range of 21 days to 28 days). This stabilized anti-NGF antibody (e.g., hinge-stabilized antibody) also exhibits a terminal elimination half life in rats of at least 8 days, typically in the range of about 8 to about 9 days (or in range of 8 to 9 days). In yet other embodiments, the stabilized anti-NGF antibody (e.g., hinge-stabilized antibody) may exhibit a mean terminal elimination half life in humans of at least 10-30 days, or at least 10 days, at least 15 days, at least 20 days, at least 25 days, at least 30 days or in a range of about 10 days to about 40 days or in a range of about 15 days to about 30 days (or in a range of 10 to 40 days or in a range of 15 to 30 days). In yet other embodiments, the stabilized anti-NGF antibody (e.g., hinge-stabilized antibody) may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks).

Preferably, the mutation in the IgG4 constant region is a hinge region mutation. Even more preferably, the hinge region mutation in the IgG4 constant region comprises mutation of the serine at the amino acid position corresponding to amino acid position 108 of SEQ ID NO: 9 (which shows the wild type amino acid sequence of the human IgG4 constant region). Accordingly, the invention provides an anti-nerve growth factor (NGF) antibody having a human IgG4 constant region, said human IgG4 constant region containing a hinge region mutation comprising the mutation of serine at the amino acid position corresponding to amino acid position 108 of SEQ ID NO: 9. More preferably, the serine at the amino acid position corresponding to amino acid position 108 of SEQ ID NO: 9 is mutated to proline. In a preferred embodiment, the human IgG4 constant region of the anti-NGF antibody comprises the amino acid sequence of SEQ ID NO: 10. Alternatively, other possible IgG4-stabilizing mutations are described herein.

A preferred anti-NGF antibody of the invention is antibody PG110, the heavy chain amino acid sequence of which is shown in SEQ ID NO: 13 and the light chain amino acid sequence of which is shown in SEQ ID NO: 16. Accordingly, the invention provides an anti-NGF antibody comprising a human IgG4 constant region, wherein the antibody comprises a heavy chain comprising the amino acid sequence of SEQ ID NO: 13 and a light chain comprising the amino acid sequence of SEQ ID NO: 16. In another embodiment, the invention provides anti-NGF antibody comprising a human IgG4 constant region, wherein the antibody comprises a heavy chain encoded by the nucleotide sequence of SEQ ID NO: 11 and a light chain encoded by the nucleotide sequence of SEQ ID NO: 14. In yet another embodiment, the invention provides an anti-NGF antibody comprising a heavy chain comprising the amino acid sequence of SEQ ID NO: 13, wherein the antibody has a terminal elimination half-life in a cynomolgus monkey of at least 15 days (and typically in the range of about 15 to about 22 days, or in a range of 15 to 22 days, or in a range of about 15 days to 28 days, or in a range of 15 to 28 days, or in the range of about 21 days to about 28 days or in range of 21 to 28 days), and/or has a terminal elimination half-life in a human of at least 10-30 days (or at least 10 days, or at least 15 days, or at least 20 days, or at least 25 days, or at least 30 days or in a range of about 10 days to about 40 days or in range of about 15 to about 30 days, or in a range of 10 to 40 days or in range of 15 to 30 days). Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks). Preferably, the heavy chain is encoded by the nucleotide sequence of SEQ ID NO: 11. Preferably, the antibody comprises a light chain comprising the amino acid sequence of SEQ ID NO: 16. Preferably, the light chain is encoded by the nucleotide sequence of SEQ ID NO: 14.

In another embodiment, the anti-NGF antibody comprises a heavy chain variable region comprising the amino acid sequence of SEQ ID NO: 1 (which shows the heavy chain variable region of PG110). In another embodiment, the anti-NGF antibody comprises a light chain variable region comprising the amino acid sequence of SEQ ID NO: 2 (which shows the light chain variable region of PG110). In yet another embodiment, the anti-NGF antibody comprises a heavy chain variable region comprising the amino acid sequence of SEQ ID NO: 1 and a light chain variable region comprising the amino acid sequence of SEQ ID NO: 2. In still another embodiment, the anti-NGF antibody competes for binding to NGF with an antibody comprising a heavy chain variable region comprising the amino acid sequence of SEQ ID NO: 1 and a light chain variable region comprising the amino acid sequence of SEQ ID NO: 2.

In another embodiment, the anti-NGF antibody comprises a heavy chain variable region comprising CDRs 1, 2 and 3 having the amino acid sequences of SEQ ID NOs: 3, 4 and 5, respectively (wherein SEQ ID NOs: 3, 4 and 5 show the heavy chain variable region CDRs 1, 2 and 3, respectively, of PG110). In another embodiment, the anti-NGF antibody comprises a light chain variable region comprising CDRs 1, 2 and 3 having the amino acid sequences of SEQ ID NOs: 6, 7 and 8, respectively (wherein SEQ ID NOs: 6, 7 and 8 show the light chain variable region CDRs 1, 2 and 3, respectively, of PG110). In still another embodiment, the anti-NGF antibody comprises a heavy chain variable region comprising CDRs 1, 2 and 3 having the amino acid sequences of SEQ ID NOs: 3, 4 and 5, respectively, and comprises a light chain variable region comprising CDRs 1, 2 and 3 having the amino acid sequences of SEQ ID NOs: 6, 7 and 8, respectively.

Preferably, the anti-NGF antibody has one or more of the following functional properties:
a) binds to human NGF but does not bind to human brain-derived neurotrophic factor (BDNF), human neurotrophin 3 (NT-3) or human neurotrophin 4 (NT-4);
b) binds to human or rat NGF with a $K_D$ of 100 pM or less;
c) inhibits binding of NGF to TrkA or $p75^{NTR}$;
d) inhibits NGF-dependent proliferation of TF-1 cells;
e) inhibits NGF-dependent chick dorsal root ganglion survival;
f) inhibits NGF-dependent PC12 cell neurite outgrowth.

In another embodiment, the anti-NGF antibody of the invention does not exhibit a rebound effect when administered to a subject. For example, a dosage amount and dosing frequency of administration for the antibody can be selected such that the antibody does not exhibit a rebound effect when administered to a subject.

In another embodiment, an anti-NGF antibody of the invention is capable of alleviating pain in a subject for a long duration, for example for a duration of at least about one week, or at least about two weeks, or at least about four weeks, or at least about eight weeks, or at least about twelve weeks, or at least about one week to about twelve weeks, or at least about four weeks to about twelve weeks, or at least about eight weeks to about twelve weeks, or for a duration of at least one week, or at least two weeks, or at least four weeks, or at least eight weeks or at least twelve weeks or at least one to twelve weeks, or at least four to twelve weeks, or at least eight to twelve weeks after administration of a single dose of the anti-NGF antibody to the subject.

In a particularly preferred embodiment, the invention provides an anti-NGF antibody that has the combined advantageous features of an extended terminal elimination half life and a prolonged duration of pain alleviation. Accordingly, the invention also provides an anti-NGF antibody comprising a human IgG4 constant region, wherein the human IgG4 constant region comprises a mutation (preferably a hinge region mutation), wherein the antibody has a terminal elimination half-life in a human of at least 10-30 days, or at least 10 days, or at least 15 days, or at least 20 days, or at least 25 days, or at least 30 days or in a range of about 10 days to about 40 days or in a range of about 15 days to about 30 days (or in a range of 10-40 days or in a range of 15-30 days), and wherein the antibody alleviates pain for a duration of at least about one week to about twelve weeks, or at least one week to twelve weeks, or at least about four weeks to about twelve weeks, or at least four weeks to twelve weeks, after administration of a single dose the antibody to a human subject (or at least one week, or at least two weeks, or at least four weeks, or at least eight weeks, or at least twelve weeks, or one to twelve weeks, or four to twelve weeks, or eight to twelve weeks, after administration of a single dose of the antibody to a human subject). Preferably, the hinge region mutation comprises mutation of the serine at the amino acid position corresponding to amino acid position 108 of SEQ ID NO: 9, preferably a serine to proline mutation at the amino acid position corresponding to amino acid position 108 of SEQ ID NO: 9. More preferably, the human IgG4 constant region comprises the amino acid sequence of SEQ ID NO: 10. In various embodiments, the antibody may exhibit one or more of the functional properties described herein. In a preferred embodiment, the antibody competes for binding to NGF with an antibody comprising a heavy chain variable region comprising the amino acid sequence of SEQ ID NO: 1 and a light chain variable region comprising the amino acid sequence of SEQ ID NO: 2.

In yet another embodiment, the invention provides an anti-nerve growth factor (NGF) antibody comprising a human IgG4 constant region, wherein the human IgG4 constant region comprises the amino acid sequence of SEQ ID NO: 10, and wherein the antibody binds to human or rat NGF with a $K_D$ of 100 pM or less, inhibits binding of NGF to TrkA or p75$^{NTR}$ with an IC$_{50}$ of 250 pM or less, and inhibits NGF-dependent proliferation of TF-1 cells with an IC$_{50}$ of 50 ng/ml or less. Preferably, the antibody has mean terminal elimination half-life in humans of at least 10-30 days, or at least 10 days, or at least 15 days, or at least 20 days, or at least 25 days, or at least 30 days or in a range of about 10 days to about 40 days or in a range of about 15 days to about 30 days (or in a range of 10-40 days or in a range of 15-30 days). Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks). The antibody may further exhibit one or more additional functional properties, such as binding to human NGF but not binding to human brain-derived neurotrophic factor (BDNF), human neurotrophin 3 (NT-3) or human neurotrophin 4 (NT-4); inhibiting NGF-dependent chick dorsal root ganglion survival; and/or inhibiting NGF-dependent PC12 cell neurite outgrowth. Preferably, the antibody alleviates pain for a duration of at least about one week to about twelve weeks, or at least about four weeks to about twelve weeks, or at least about eight weeks to about twelve weeks, or at least one week to twelve weeks, or at least four weeks to twelve weeks or at least eight weeks to twelve weeks (or at least one week, or at least four weeks, or at least eight weeks, or at least twelve weeks, or for one to twelve weeks, or for four to twelve weeks, or for eight to twelve weeks) after administration of a single dose the anti-NGF antibody to a subject. Preferably, the antibody comprises a heavy chain variable region comprising CDRs 1, 2 and 3 having the amino acid sequences of SEQ ID NOs: 3, 4 and 5, respectively, or the antibody comprises a light chain variable region comprising CDRs 1, 2 and 3 having the amino acid sequences of SEQ ID NOs: 6, 7 and 8, respectively, or the antibody comprises a heavy chain variable region comprising CDRs 1, 2 and 3 having the amino acid sequences of SEQ ID NOs: 3, 4 and 5, respectively, and a light chain variable region comprising CDRs 1, 2 and 3 having the amino acid sequences of SEQ ID NOs: 6, 7 and 8, respectively. Preferably, the antibody comprises a heavy chain variable region comprising the amino acid sequence of SEQ ID NO: 1 or the antibody comprises a light chain variable region comprising the amino acid sequence of SEQ ID NO: 2, or the antibody comprises a heavy chain variable region comprising the amino acid sequence of SEQ ID NO: 1 and a light chain variable region comprising the amino acid sequence of SEQ ID NO: 2, or the antibody competes for binding to NGF with an antibody comprising a heavy chain variable region comprising the amino acid sequence of SEQ ID NO: 1 and a light chain variable region comprising the amino acid sequence of SEQ ID NO: 2.

In various preferred embodiments, the invention provides anti-NGF antibodies having the following features:

An anti-nerve growth factor (NGF) antibody comprising (i) a heavy chain variable region comprising CDRs 1, 2 and 3 having the amino acid sequences of SEQ ID NOs: 3, 4 and 5, respectively, (ii) a light chain variable region comprising CDRs 1, 2 and 3 having the amino acid sequences of SEQ ID NOs: 6, 7 and 8, respectively, and (iii) a human IgG4 constant region, wherein the human IgG4 constant region comprises the amino acid sequence of SEQ ID NO: 10, wherein the antibody has a mean terminal elimination half-life in humans of at least 10-30 days. Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks).

An anti-nerve growth factor (NGF) antibody comprising (i) a heavy chain variable region comprising the amino acid sequence of SEQ ID NO:1, (ii) a light chain variable region comprising the amino acid sequence of SEQ ID NO: 2, and (iii) a human IgG4 constant region, wherein the human IgG4 constant region comprises the amino acid sequence of SEQ ID NO: 10, wherein the antibody has a mean terminal elimination half-life in humans of at least 10-30 days. Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks).

An anti-nerve growth factor (NGF) antibody comprising (i) a heavy chain variable region comprising CDRs 1, 2 and 3 having the amino acid sequences of SEQ ID NOs: 3, 4 and 5, respectively, (ii) a light chain variable region comprising CDRs 1, 2 and 3 having the amino acid sequences of SEQ ID NOs: 6, 7 and 8, respectively, and (iii) a human IgG4 constant region comprising a hinge region mutation, wherein the antibody has a mean terminal elimination half-life in humans of at least 10-30 days. Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks).

An anti-nerve growth factor (NGF) antibody comprising (i) a heavy chain variable region comprising the amino acid sequence of SEQ ID NO:1, (ii) a light chain variable region comprising the amino acid sequence of SEQ ID NO: 2, and (iii) a human IgG4 constant region comprising a hinge region mutation, wherein the antibody has a mean terminal elimination half-life in humans of at least 10-30 days. Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks).

An anti-nerve growth factor (NGF) antibody comprising (i) a heavy chain variable region comprising CDRs 1, 2 and 3 having the amino acid sequences of SEQ ID NOs: 3, 4 and 5, respectively, (ii) a light chain variable region comprising CDRs 1, 2 and 3 having the amino acid sequences of SEQ ID NOs: 6, 7 and 8, respectively, and (iii) a constant region comprising a hinge region mutation, wherein the antibody has a mean terminal elimination half-life in humans of at least 10-30 days. Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks).

An anti-nerve growth factor (NGF) antibody comprising (i) a heavy chain variable region comprising the amino acid sequence of SEQ ID NO:1, (ii) a light chain variable region comprising the amino acid sequence of SEQ ID NO: 2, and (iii) a constant region comprising a hinge region mutation, wherein the antibody has a mean terminal elimination half-life in humans of at least 10-30 days. Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks).

An anti-nerve growth factor (NGF) antibody comprising a human IgG4 constant region, wherein the human IgG4 constant region comprises the amino acid sequence of SEQ ID NO: 10, wherein the antibody binds to human or rat NGF with a $K_D$ of 100 pM or less, inhibits binding of NGF to TrkA or p75$^{NTR}$ with an $IC_{50}$ of 250 pM or less, and inhibits NGF-dependent proliferation of TF-1 cells with an $IC_{50}$ of 50 ng/ml or less, and wherein the antibody has a mean terminal elimination half-life in humans of at least 10-30 days. Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks).

An anti-nerve growth factor (NGF) antibody comprising (i) a heavy chain variable region comprising CDRs 1, 2 and 3 having the amino acid sequences of SEQ ID NOs: 3, 4 and 5, respectively, (ii) a light chain variable region comprising CDRs 1, 2 and 3 having the amino acid sequences of SEQ ID NOs: 6, 7 and 8, respectively, and (iii) a human IgG4 constant region, wherein the human IgG4 constant region comprises the amino acid sequence of SEQ ID NO: 10, wherein the antibody binds to human or rat NGF with a $K_D$ of 100 pM or less, inhibits binding of NGF to TrkA or p75$^{NTR}$ with an $IC_{50}$ of 250 pM or less, and inhibits NGF-dependent proliferation of TF-1 cells with an $IC_{50}$ of 50 ng/ml or less.

An anti-nerve growth factor (NGF) antibody comprising (i) a heavy chain variable region comprising the amino acid sequence of SEQ ID NO:1, (ii) a light chain variable region comprising the amino acid sequence of SEQ ID NO: 2, and (iii) a human IgG4 constant region, wherein the human IgG4 constant region comprises the amino acid sequence of SEQ ID NO: 10, wherein the antibody binds to human or rat NGF with a $K_D$ of 100 pM or less, inhibits binding of NGF to TrkA or p75$^{NTR}$ with an $IC_{50}$ of 250 pM or less, and inhibits NGF-dependent proliferation of TF-1 cells with an $IC_{so}$ of 50 ng/ml or less.

An anti-nerve growth factor (NGF) antibody comprising (i) a heavy chain variable region comprising CDRs 1, 2 and 3 having the amino acid sequences of SEQ ID NOs: 3, 4 and 5, respectively, (ii) a light chain variable region comprising CDRs 1, 2 and 3 having the amino acid sequences of SEQ ID NOs: 6, 7 and 8, respectively, and (iii) a human IgG4 constant region, comprising a hinge region mutation, wherein the antibody binds to human or rat NGF with a $K_D$ of 100 pM or less, inhibits binding of NGF to TrkA or p75$^{NTR}$ with an $IC_{so}$ of 250 pM or less, and inhibits NGF-dependent proliferation of TF-1 cells with an $IC_{so}$ of 50 ng/ml or less.

An anti-nerve growth factor (NGF) antibody comprising (i) a heavy chain variable region comprising the amino acid sequence of SEQ ID NO:1, (ii) a light chain variable region comprising the amino acid sequence of SEQ ID NO: 2, and (iii) a human IgG4 constant region comprising a hinge region mutation, wherein the antibody binds to human or rat NGF with a $K_D$ of 100 pM or less, inhibits binding of NGF to TrkA or p75$^{NTR}$ with an $IC_{50}$ of 250 pM or less, and inhibits NGF-dependent proliferation of TF-1 cells with an $IC_{so}$ of 50 ng/ml or less.

An anti-nerve growth factor (NGF) antibody comprising (i) a heavy chain variable region comprising CDRs 1, 2 and 3 having the amino acid sequences of SEQ ID NOs: 3, 4 and 5, respectively, (ii) a light chain variable region comprising CDRs 1, 2 and 3 having the amino acid sequences of SEQ ID NOs: 6, 7 and 8, respectively, and (iii) a constant region comprising a hinge region mutation, wherein the antibody binds to human or rat NGF with a $K_D$ of 100 pM or less, inhibits binding of NGF to TrkA or p75$^{NTR}$ with an $IC_{50}$ of 250 pM or less, and inhibits NGF-dependent proliferation of TF-1 cells with an $IC_{50}$ of 50 ng/ml or less.

An anti-nerve growth factor (NGF) antibody comprising (i) a heavy chain variable region comprising the amino acid sequence of SEQ ID NO:1, (ii) a light chain variable region comprising the amino acid sequence of SEQ ID NO: 2, and (iii) a constant region comprising a hinge region mutation, wherein the antibody binds to human or rat NGF with a $K_D$ of 100 pM or less, inhibits binding of NGF to TrkA or p75$^{NTR}$ with an $IC_{so}$ of 250 pM or less, and inhibits NGF-dependent proliferation of TF-1 cells with an $IC_{50}$ of 50 ng/ml or less.

An anti-nerve growth factor (NGF) antibody comprising a human IgG4 constant region, wherein the human IgG4 constant region comprises a mutation, and wherein the antibody has a mean terminal elimination half-life in humans of at least 10-30 days. Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks).

An anti-nerve growth factor (NGF) antibody comprising a human IgG4 constant region, wherein the human IgG4 constant region comprises a mutation and wherein the antibody has a terminal elimination half-life in a cynomolgus monkey of at least 15 days. Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks).

In various embodiments, the anti-NGF antibody of the invention can be, for example, a chimeric, a humanized or a human antibody, or an antibody in which the potential T cell epitopes have been eliminated.

In another aspect, the invention provides a pharmaceutical composition comprising an anti-NGF antibody of the invention and a pharmaceutically acceptable carrier.

In yet another aspect, the invention provides a method of attenuating or inhibiting an NGF-related disease or condition in a subject, the method comprising administering to the subject an anti-NGF antibody of the invention. Non-limiting examples of NGF-related diseases and conditions include inflammatory pain, post-operative pain, neuropathic pain, fracture pain, gout joint pain, post-herpetic neuralgia, cancer pain, osteoarthritis or rheumatoid arthritis pain, sciatica, pains associated with sickle cell crises, headaches, dysmenorrhea, endometriosis, musculoskeletal pain, chronic low back pain, fibromyalgia, sprains, visceral pain, ovarian cysts, prostatitis, cystitis, interstitial cystitis, incisional pain, migraine, trigeminal neuralgia, pain from burns and/or wounds, pain associated with trauma, pain associated with musculoskeletal diseases, ankylosing spondilitis, periarticular pathologies, pain from bone metastases, pain from HIV, erythromelalgia or pain caused by pancreatitis or kidney stones. Other examples of NGF-related diseases and conditions include malignant melanoma, Sjogren's syndrome and asthma, such as uncontrolled asthma with severe airway hyper-responsiveness, and intractable cough. Particularly preferred diseases and conditions for treatment according to the methods of the invention include inflammatory pain (particularly osteoarthritis or rheumatoid arthritis pain), musculoskeletal pain (particularly chronic low back pain), neuropathic pain (particularly diabetic neuropathy), cancer pain and pain from bone metastases, interstitial cystitis/painful bladder syndrome, pain associated with chronic abacterial prostatitis, pain associated with endometriosis and/or uterine fibroids and post-operative pain.

The antibody can be administered, for example, intravenously, subcutaneously (e.g., via an injection pen or subcutaneous implant), intramuscularly or intra-articularly, although other suitable routes of administration are described herein. Preferably, the antibody is administered at a dose in a range of 0.1 mg/kg to 3 mg/kg or at a dose in a range of 0.1 mg/kg to 30 mg/kg. The antibody can be administered, for example, at a dose in a range from about 3 µg/kg to about 3000 µg/kg, with preferred dosages including 100 µg/kg or 300 µg/kg, In other embodiments, the antibody is administered at a dose in a range of 0.1 mg/kg to 30 mg/kg, or in a range of 0.1 mg/kg to 20 mg/kg, or in a range of 0.1 mg/kg to 10 mg/kg, or in a range of 1 mg/kg to 30 mg/kg, or in a range of 1 mg/kg to 20 mg/kg or in a range of 1 mg/kg to 10 mg/kg, although other suitable dosages and dose ranges are described herein. Furthermore, a fixed dose formulation of the antibody can be used.

The antibody can be administered alone or in combination with one or more additional pharmaceutical agents. For example, a second pharmaceutical agent, such as an NSAID, an analgesic (e.g., an opioid analgesic), a local anaesthetic, a nerve block, a phenol block, a therapeutic antibody, an anticonvulsant, an anti-depressant, topical capsaicin, a steroid or an antiviral agent, can be administered in combination with the anti-NGF antibody of the invention. Particularly preferred second pharmaceutical agents for combination treatment with an antibody of the invention include opioid analgesics, such as morphine and the like. Other preferred second pharmaceutical agents for combination treatment include TrkA inhibitors and Protein Kinase C (PKC) inhibitors.

In a preferred embodiment, the invention provides a method of attenuating or inhibiting pain in a subject, the method comprising administering to the subject an anti-nerve growth factor (NGF) antibody comprising a human IgG4 constant region, wherein the human IgG4 constant region comprises the amino acid sequence of SEQ ID NO: 10, and wherein the antibody alleviates pain in the subject for a duration of at least four to twelve weeks (or for at least one to twelve weeks, or for at least eight to twelve weeks, or for four to twelve weeks, or for one to twelve weeks, or for eight to twelve weeks, or for at least one week, or for at least four weeks, or for at least eight weeks, or for at least twelve weeks) after administration of a single dose of the anti-NGF antibody to a subject. Preferably, the anti-NGF antibody comprises a heavy chain variable region comprising CDRs 1, 2 and 3 having the amino acid sequences of SEQ ID NOs: 3, 4 and 5, respectively, and a light chain variable region comprising CDRs 1, 2 and 3 having the amino acid sequences of SEQ ID NOs: 6, 7 and 8, respectively. Preferably, the anti-NGF antibody comprises a heavy chain variable region comprising the amino acid sequence of SEQ ID NO: 1 and a light chain variable region comprising the amino acid sequence of SEQ ID NO: 2. Preferably, the pain is selected from the group consisting of osteoarthritis pain, chronic low back pain, diabetic neuropathic pain, cancer pain, pain from bone metastases, interstitial cystitis, painful bladder syndrome, pain associated with chronic abacterial prostatitis, pain associated with endometriosis, pain associated with uterine fibroids and post-operative pain. Preferably, the anti-NGF antibody is administered at a dose in a range from 0.1 to 3 mg/kg or at a dose in a range from 0.1 mg/kg to 30 mg/kg. Preferably, the antibody is administered intravenously or subcutaneously. Preferably, the antibody has a terminal elimination half-life in a human of at least 10-30 days (or at least 10 days, or at least 15 days, or at least 20 days, or at least 25 days, or at least 30 days or in a range of about 10 days to about 40 days or in range of about 15 to about 30 days, or in a range of 10 to 40 days or in range of 15 to 30 days).

In another preferred embodiment, the invention provides a method of attenuating or inhibiting a nerve growth factor (NGF)-related disease or condition in a subject such that a rebound effect is avoided in the subject, the method comprising administering to the subject an anti-NGF antibody comprising a human IgG4 constant region, wherein the human IgG4 constant region comprises a hinge region mutation, and wherein the antibody has a terminal elimination half-life in a human of at least 10-30 days (or at least 10 days, or at least 15 days, or at least 20 days, or at least 25 days, or at least 30 days or in a range of about 10 days to about 40 days or in range of about 15 to about 30 days, or in a range of 10 to 40 days or in range of 15 to 30 days), and wherein the antibody is administered at a dosage and at a frequency such that a rebound effect is avoided in the subject. Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks). Preferably, the human IgG4 constant region comprises a mutation at the amino acid position corresponding to amino acid position 108 of SEQ ID NO: 9. Preferably, the serine at the amino acid position corresponding to amino acid position 108 of SEQ ID NO: 9 is mutated to proline. Preferably, the human IgG4 constant region comprises the amino acid sequence of SEQ ID NO: 10. Preferably, the anti-NGF antibody comprises a heavy chain variable region comprising CDRs 1, 2 and 3 having the amino acid sequences of SEQ ID NOs: 3, 4 and 5, respectively, and a light chain variable region comprising CDRs 1, 2 and 3 having the amino acid sequences of SEQ ID NOs: 6, 7 and 8, respectively. Preferably, the anti-NGF antibody comprises a heavy chain variable region comprising the amino acid sequence of SEQ ID NO: 1 and a light chain variable region comprising the amino acid sequence of SEQ ID NO: 2. Preferably, the antibody competes for binding to NGF with an antibody comprising a heavy chain variable region comprising the amino acid sequence of SEQ ID NO: 1 and a light chain variable region comprising the amino acid sequence of SEQ ID NO: 2. Preferably, the NGF-related disease or condition is pain selected from the group consisting of osteoarthritis pain, chronic low back pain, diabetic neuropathic pain, cancer pain, pain from bone metastases, interstitial cystitis, painful bladder syndrome, pain associated with chronic abacterial prostatitis, pain associated with endometriosis, pain associated with uterine fibroids and post-operative pain. Preferably, the anti-NGF antibody is administered at a dose in a range from 0.1 to 3 mg/kg or in a range from 0.1 mg/kg to 30 mg/kg. Preferably, the antibody is administered intravenously or subcutaneously.

In another aspect, the invention provides for the use of the anti-NGF antibody of the invention for the manufacture of a medicament for use to attenuate or inhibit an NGF-related disease or condition in a subject. Non-limiting examples of NGF-related diseases and conditions include those set forth above. A preferred NGF-related disease or condition is pain. Preferably, the pain is selected from the group consisting of osteoarthritis pain, chronic low back pain, diabetic neuropathic pain, cancer pain, pain from bone metastases, interstitial cystitis, painful bladder syndrome, pain associated with chronic abacterial prostatitis, pain associated with endometriosis, pain associated with uterine fibroids and post-operative pain.

In another aspect, the invention provides for use of the anti-NGF antibody of the invention for the manufacture of a medicament for use to attenuate or inhibit pain in a subject, such that pain is attenuated or inhibited in the subject for a duration of at least about one week to about twelve weeks, or at least about four weeks to about twelve weeks, or at least about eight weeks to about twelve weeks (or for a duration of one to twelve weeks, or four to twelve weeks, or eight to twelve weeks, or at least one week, or at least two weeks, or at least four weeks, or at least eight weeks, or at least twelve weeks) after administration of a single dose of the anti-NGF antibody to a subject.

In another aspect, the invention provides for use of the anti-NGF antibody of the invention for the manufacture of a medicament for use to attenuate or inhibit an NGF-related disease or condition in a subject such that a rebound effect is avoided in the subject. In particular, the antibody is administered at a dosage and at a frequency such that a rebound effect is avoided in the subject.

In still other aspects, the invention provides nucleic acid molecules encoding the heavy chains and/or light chains of the anti-NGF antibodies of the invention, as well as vectors (e.g., expression vectors) comprising such vectors, host cells comprising such vectors and methods for expressing the anti-NGF antibodies using the host cells of the invention.

In another aspect, the invention provides a method of attenuating or inhibiting a nerve growth factor (NGF)-related disease or condition in a subject such that a rebound effect is avoided in the subject. The method comprises administering to the subject an anti-NGF antibody comprising a human IgG4 constant region, wherein the human IgG4 constant region comprises a mutation (preferably a hinge region mutation) and wherein the antibody has a terminal elimination half-life in a cynomolgus monkey of at least 15 days, more preferably of at least 21 days, and wherein the antibody is administered at a dosage and at a frequency such that a rebound effect is avoided in the subject. In another embodiment, the antibody has a terminal elimination half-life in a cynomolgus monkey in a range of about 15 days to about 22 days (or 15-22 days), or a range of about 15 days to about 28 days (or 15-28 days), or in a range of about 21 days to about 28 days (or 21-28 days). In another embodiment, the antibody has a terminal elimination half-life in a rat of at least 8 days. In yet another embodiment, the antibody has a mean terminal elimination half-life in humans of at least 10-30 days (or at least 10 days, or at least 15 days, or at least 20 days, or at least 25 days, or at least 30 days, or in a range of about 10 days to about 40 days, or in a range of about 15 to about 30 days, or in a range of 10-40 days or in a range of 15-30 days). Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks). Preferred mutations include those described above. Preferred antibodies include those having the sequences and/or the additional functional properties as described above. Non-limiting examples of NGF-related diseases and conditions include those set forth above.

The invention also provides for the use of the anti-NGF antibody of the invention for the manufacture of a medicament for use to attenuate or inhibit an NGF-related disease or condition in a subject such that a rebound effect is avoided in the subject.

Kits comprising an anti-NGF antibody of the invention are also provided herein. For example, a kit may comprise anti-NGF antibody and instructions for use of the antibody in treating an NGF-related disease or condition.

DETAILED DESCRIPTION OF THE INVENTION

Figure 1:
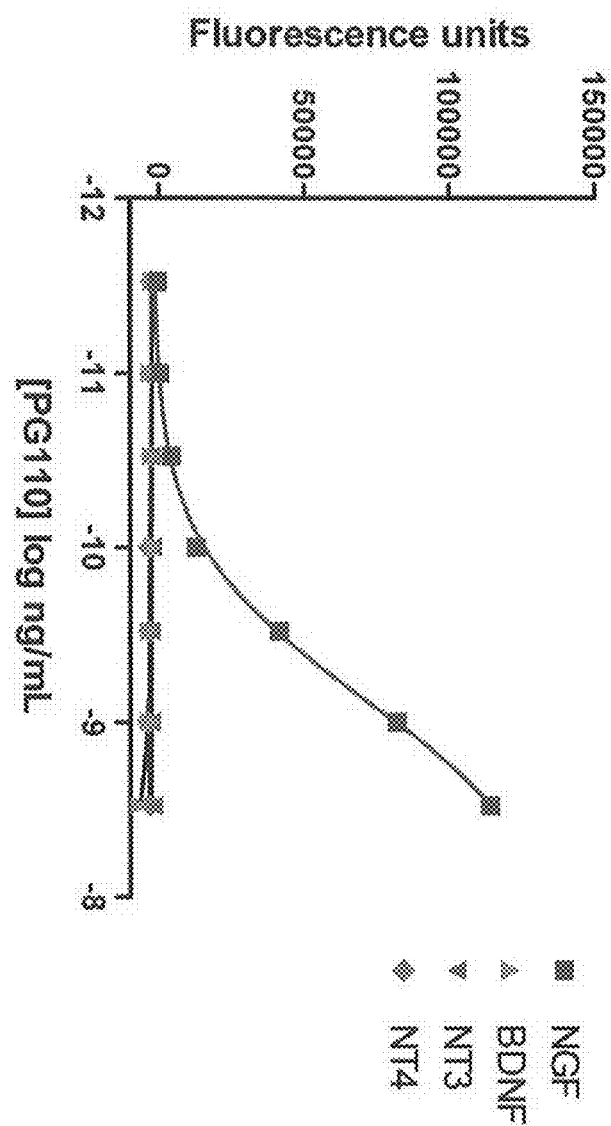
FIG. 1 is a graph showing the binding of PG110 to human nerve growth factor (NGF) but not to human brain derived neurotrophic factor (BDNF), human neurotrophin 3 (NT-3) or human neurotrophin 4 (NT-4), as determined by ELISA.

The invention pertains to anti-nerve growth factor antibodies that exhibit enhanced in vivo stability, as evidenced by, for example, an unexpectedly long terminal elimination half life in cynomolgus monkeys. The antibodies of the invention include a modification of the human IgG4 constant region of the antibody, by introduction of a mutation into the IgG4 constant region, preferably into the hinge region of the constant region.

In order that the present invention may be more readily understood, certain terms are first defined. Additional definitions are set forth throughout the detailed description.

I. DEFINITIONS

The terms "nerve growth factor" or "NGF" are used interchangeably herein and includes variants, isoforms, homologs, orthologs and paralogs. For example, an antibody specific for human NGF may, in certain cases, cross-react with NGF from species other than human. In other embodiments, an antibody specific for human NGF may be completely specific for human NGF and may not exhibit species or other types of cross-reactivity. The term "human NGF" refers to human sequence NGF, such as comprising the amino acid sequence of human NGF-β chain, the precursor form of which has Genbank accession number NP_002497, encoded by the nucleotide sequence of Genbank accession number NM_002506. The human NGF-13 chain sequence may differ from human NGF-13 of Genbank Accession No. NP_002497 by having, for example, conserved substitutions or substitutions in non-conserved regions wherein the human NGF-13 has substantially the same biological function as the human NGF-13 of Genbank Accession No. NP_002497. The term "rat NGF" refers to rat sequence NGF, such as comprising the amino acid sequence of rat NGF-β chain, the precursor form of which has Genbank accession number XP_227525, encoded by the nucleotide sequence of Genbank accession number XP_227525. The term "mouse NGF" refers to rat sequence NGF, such as comprising the amino acid sequence of mouse NGF-13 chain, the precursor form of which has Genbank accession number NP_038637, encoded by the nucleotide sequence of Genbank accession number NM_013609.

The term "TrkA receptor", as used herein, refers to an NGF receptor also known in the art as tropomyosin kinase receptor A and neurotrophic tyrosine kinase receptor type 1 (NTRK1). Exemplary, non-limiting sequences for human TrkA receptor include the amino acid sequences of Genbank accession number NP_001012331 (isoform 1), NP_002520 (isoform 2) and NP_001007793 (isoform 3).

The term "p75$^{NTR}$ receptor", as used herein refers to a neurotrophin receptor, with a molecular weight of approximately 75 kDa, that binds NGF and other neurotrophins, which receptor is described in, e.g., Bothwell, M. (1996) *Science* 272:506-507. An exemplary, non-limiting sequence for human p75$^{NTR}$ receptor is the amino acid sequence of Genbank accession number NP_002498, encoded by the nucleotide sequence of Genbank accession number NM_002507.

The term "terminal elimination half life", as used herein with regard to the anti-NGF antibodies, refers to the amount of time needed for the concentration of the antibody, as measured in the serum of a subject to which the antibody has been administered, to be reduced by half once both absorption and redistribution of the antibody are complete. When a group of subjects is used, the geometric mean of the terminal elimination half life in the subjects can be used as the measure of the terminal elimination half life of the antibody.

The term "pharmacologic half life", as used herein with regard to the anti-NGF antibodies, refers to the average amount of time to maintain drug effect in vivo (MRT for drug effect). It can be calculated as the ratio of area of the first moment baseline-corrected effect-time curve (AUMEC) vs. accumulated baseline-corrected drug effect over time (area under the effect-time curve, AUEC), using the following formula:

$$\text{Pharmacologic Half-life} = \frac{AUMEC}{AUEC} = \frac{\int E(t)t\,dt}{\int E(t)\,dt}$$

When a group of subjects is used, the geometric mean of the pharmacologic half life in the subjects can be used as the measure of the pharmacologic half life of the antibody.

The term "hinge region mutation", as used herein, refers to a mutation, such as a point mutation, substitution, addition or deletion, in the hinge region of an immunoglobulin constant domain.

The term "inhibition" as used herein, refers to any statistically significant decrease in biological activity, including full blocking of the activity. For example, "inhibition" can refer to a decrease of about 10%, 20%, 30%, 40%, 50%, 60%, 70%, 80%, 90%, or 100% in biological activity.

The term "antibody" or "immunoglobulin," as used interchangeably herein, includes whole antibodies and any antigen binding fragment (i.e., "antigen-binding portion") or single chains thereof that retains the enhanced in vivo stability described herein. An "antibody" comprises at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies can be prepared using any art recognized technique, for example, a hybridoma method, as described by Kohler et al. (1975) *Nature*, 256:495, a transgenic animal, as described by, for example, (see e.g., Lonberg, et al. (1994) Nature 368(6474): 856-859), recombinant DNA methods (see, e.g., U.S. Pat. No. 4,816,567), or using phage antibody libraries using the techniques described in, for example, Clarkson et al., Nature, 352:624-628 (1991) and Marks et al., *J. Mol. Biol.*, 222:581-597 (1991). Monoclonal antibodies include chimeric antibodies, human antibodies and humanized antibodies and may occur naturally or be recombinantly produced.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The term "humanized antibody" or "humanized immunoglobulin" refers to an antibody or immunoglobulin that includes at least one humanized antibody or immunoglobulin chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The term "human antibody," as used herein, is intended to include antibodies having variable regions in which both the framework and CDR regions are derived from human germline immunoglobulin sequences as described, for example, by Kabat et al. (See Kabat, et al. (1991) *Sequences of proteins of Immunological Interest, Fifth Edition*, U.S. Department of Health and Human Services, NIH Publication No. 91-3242). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

An "isolated antibody," as used herein, is intended to refer to an antibody which is substantially free of other antibodies having different antigenic specificities (e.g., an isolated antibody that specifically binds to NGF is substantially free of antibodies that specifically bind antigens other than NGF). In addition, an isolated antibody is typically substantially free of other cellular material and/or chemicals.

As used herein, the terms "specific binding," "specifically binds," "selective binding," and "selectively binds," mean that an antibody or antigen-binding portion thereof, exhibits appreciable affinity for a particular antigen or epitope and, generally, does not exhibit significant cross-reactivity with other antigens and epitopes. "Appreciable" or preferred binding includes binding with an affinity of at least $10^6$, $10^7$, $10^8$, $10^9$ M$^{-1}$, or $10^{10}$ M$^{-1}$. Affinities greater than $10^7$ M$^{-1}$, preferably greater than $10^8$ M$^{-1}$ are more preferred. Values intermediate of those set forth herein are also intended to be within the scope of the present invention and a preferred binding affinity can be indicated as a range of affinities, for example, $10^6$ to $10^{10}$ M$^{-1}$, preferably $10^7$ to $10^{10}$ M$^{-1}$, more preferably $10^8$ to $10^{10}$ M$^{-1}$. An antibody that "does not exhibit significant cross-reactivity" is one that will not appreciably bind to an undesirable entity (e.g., an undesirable proteinaceous entity). Specific or selective binding can be determined according to any art-recognized means for determining such binding, including, for example, according to Scatchard analysis and/or competitive binding assays.

The term "$K_D$," as used herein, is intended to refer to the dissociation equilibrium constant of a particular antibody-antigen interaction or the affinity of an antibody for an antigen. In one embodiment, the antibody according to the present invention binds an antigen (e.g., NGF) with an affinity ($K_D$) of about 100 pM or less (i.e., or better) (e.g., about 90 pM or about 80 pM or about 70 pM or about 60 pM or about 50 pM or about 40 pM or about 30 pM), as measured using a surface plasmon resonance assay or a cell binding assay. In a preferred embodiment, the antibody binds NGF with an affinity ($K_D$) in a range of about 25-35 pM.

The term "$K_{ass}$", as used herein, is intended to refer to the association rate constant for the association of an antibody into the antibody/antigen complex.

The term "$K_{diss}$", as used herein, is intended to refer to the dissociation rate constant for the dissociation of an antibody from the antibody/antigen complex.

The term "$IC_{50}$", as used herein, refers to the concentration of an antibody that inhibits a response, either in an in vitro or an in vivo assay, to a level that is 50% of the maximal inhibitory response, i.e., halfway between the maximal inhibitory response and the untreated response.

The term "nucleic acid molecule," as used herein, is intended to include DNA molecules and RNA molecules. A nucleic acid molecule may be single-stranded or double-stranded, but preferably is double-stranded DNA. The term "isolated nucleic acid molecule," as used herein in reference to nucleic acids encoding antibodies or antibody portions (e.g., $V_H$, $V_L$, CDR3) that bind to NGF, is intended to refer to a nucleic acid molecule in which the nucleotide sequences encoding the antibody or antibody portion are free of other nucleotide sequences encoding antibodies that bind antigens other than NGF, which other sequences may naturally flank the nucleic acid in human genomic DNA.

The term "operably linked" refers to a nucleic acid sequence placed into a functional relationship with another nucleic acid sequence. For example, DNA for a signal sequence or secretory leader sequence is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "treat," "treating," and "treatment," as used herein, refer to therapeutic or preventative measures described herein. The methods of "treatment" employ administration, to a subject, of an antibody of the present invention, for example, a subject having an NGF-related disease or condition, in order to prevent, cure, delay, reduce the severity of, or ameliorate one or more symptoms of the disease or condition.

The term "NGF-related disease or condition", as used herein, refers to diseases and conditions in which NGF activity is involved with, or associated with, or mediates or promotes one or more symptoms of the disease or condition.

As used herein, the term "subject" includes any human or non-human animal. In a particular embodiment, the subject is a human. The term "non-human animal" includes all vertebrates, e.g., mammals and non-mammals, such as non-human primates, sheep, dog, cow, chickens, amphibians, reptiles, etc.

As used herein, the term "rebound effect" refers to diminished efficacy of NGF sequestering agents, such as an anti-NGF antibody, occurring in a subject after an initial period of effectiveness after single or repeat administration. For example, treatment with an anti-NGF antibody may initially relieve pain, e.g. due to inflammation or nerve damage or other ethiology, which is then followed by a period of diminished analgesic efficacy in which pain eventually becomes about as intense or more intense than before treatment. In another example, an anti-NGF antibody may exhibit an initial effectiveness in a subject for a period of time after single or repeat administration, such as a period of one week after administration (e.g., days 1-7 after administration), which is then followed by a period of diminished efficacy, such as for a period from 1-2 weeks after administration (e.g., days 7-14 after administration). This "rebound" period may be followed by a period of recovery of efficacy of the anti-NGF antibody. For example, there can be a biphasic profile of analgesia after single or repeat administration of an anti-NGF antibody, with an intermediate period of reduced efficacy or even exaggerated pain sensation. This rebound effect can be assessed in, for example, clinical pain studies, experimental models of pain and/or other models of anti-NGF efficacy. This rebound effect can be associated with, for example, increased pain in the subject and/or increased adverse events (such as abnormal sensations, ranging from allodynia to dysesthesia, paresthesia and hyper- or hypoesthesia) during the rebound period. Although not intending to be limited by mechanism, the rebound effect may be caused by altered NGF expression, altered TrkA or p75 receptor expression or signaling or any other mechanism that results in transient diminished efficacy after single or repeat administration of an anti-NGF after an initial period of efficacy.

Various aspects of the invention are described in further detail in the following subsections.

II. ANTIBODIES OF THE INVENTION

A. Enhanced In Vivo Stability

The anti-NGF antibodies of the invention are characterized by having enhanced in vivo stability, as evidenced by the long terminal elimination half life observed in vivo. Although not intending to be limited by mechanism, it is thought that the extended terminal elimination half life of the antibody results from a reduced clearance rate of the antibody rather than from an increase in the distribution volume of the antibody. The antibodies of the invention comprise a human IgG4 constant region that comprises a mutation. A preferred mutation is a hinge region mutation. Preferably, the hinge region mutation comprises mutation of serine at amino acid position 108 of SEQ ID NO: 9 (wherein SEQ ID NO: 9 shows the amino acid sequence of the wild-type human IgG4 constant region). More preferably, the hinge region mutation comprises mutation of the serine at amino acid position 108 of SEQ ID NO: 9 to proline. In a preferred embodiment, the human IgG4 constant region comprises the amino acid sequence of SEQ ID NO: 10.

An anti-NGF antibody of the invention exhibits an unexpectedly long terminal elimination half life, such as a terminal elimination half life in a cynomolgus monkey of at least 15 days and typically in the range of about 15 to about 22 days (or in a range of 15-22 days), or in a range of about 15 days to about 28 days (or in a range of 15-28 days) or in a range of about 21 days to about 28 days (or in a range of 21-28 days). This stabilized anti-NGF antibody also exhibits a terminal elimination half life in rats of at least 8 days, typically in the range of about 8 to about 9 days (or in a range of 8-9 days). As described in detail in Example 4, PG110, an anti-NGF antibody of the invention, exhibits a mean terminal elimination half life in cynomolgus monkeys of at least 15 days and typically longer. For example, in one cynomolgus monkey study, a mean terminal elimination half life in a range of about 15 to about 22 days was observed. In another cynomolgus monkey study, a mean terminal elimination half life in a range of about 21 to about 28 days was observed. Furthermore, PG110 exhibits a mean terminal elimination half life in rats of about 8 to about 9 days. Still further, as it is known in the art that the terminal elimination half life of IgG in humans is about twice that of monkeys, it is predicted that the anti-NGF antibodies of the invention, such as PG110, will have terminal elimination half life in humans of at least 10-30 days, or at least 10 days, or at least 15 days, or at least 20 days, or at least 25 days, or more preferably at least 30 days or at least 40 days, or in a range of about 10 days to about 40 days (or in range of 10-40 days) or in a range of about 15 to about 30 days (or in a range of 15-30 days). Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks). As described further in Example 8, an anti-NGF antibody of the invention of the invention has been shown to have a mean pharmacologic half life in humans in the aforementioned ranges.

The terminal elimination half life for PG110 in cynomolgus monkeys is considerably longer than the half life that has been reported in the art for other IgG4 antibodies in cynomolgus monkeys. For example, a half life of about 40-90 hours (about 1.6-3.8 days) in cynomolgus monkeys has been reported for CDP571, an IgG4 anti-TNF antibody (see Stephens, S. et al. (1995) *Immunol.* 85:668-674). Similarly, a half life of about 3 days in cynomolgus monkeys has been reported for natalizumab, an IgG4 anti-integrin antibody (see Refusal CHMP Assessment Report for Natalizumab, European Medicines Agency, London, 15 Nov. 2007, Doc. Ref. EMEA/CHMP/8203/2008).

A preferred hinge region mutation used in the invention is a serine to proline mutation at position 108 in SEQ ID NO: 9. This mutation has been previously described in the art (see Angal, S. et al. (1993) *Mol. Immunol.* 30:105-108) and reported to abolish the heterogeneity of IgG4 molecules, in particular the formation of half antibodies containing a single heavy chain and a single light chain. Accordingly, substitution of an amino acid other than proline at position 108 of SEQ ID NO: 9 also is encompassed by the invention, wherein the substitution achieves the same effect as the Ser to Pro mutation in eliminating the heterogeneity of the IgG4 molecule (e.g., the formation of half antibodies). The ability of a mutation at position 108 to eliminate the heterogeneity of the IgG4 molecule can be assessed as described in Angal et al. (1993), supra.

In addition to, or alternative to, the modification at position 108 of SEQ ID NO: 9, other IgG hinge region mutations have been described that improve the affinity of the FcRn-IgG interaction, resulting in an extended half life for the modified IgG. Examples of such additional or alternative modifications include mutations at one or more IgG constant region residues corresponding to: Thr250, Met252, Ser254, Thr256, Thr307, Glu308, Met428, His 433 and/or Asn434 (as described further in Shields, R. L. et al. (2001) *J. Biol. Chem.* 276:6591-6604; Petkova, S. B. et al. (2006) *Int. Immunol.* 18:1759-1769; Hinton, P. R. et al. (2004) *J. Biol. Chem.* 279:6213-6216; Kamei, D. T. et al. (2005) *Biotechnol. Bioeng.* 92:748-760; Vaccaro, C. et al. (2005) *Nature Biotechnol.* 23:1283-1288; Hinton, P. R. et al. (2006) *J. Immunol.* 176:346-356).

Still further, alternative to hinge region mutations, other stabilizing modifications of the IgG4 constant region have been described. For example, in other embodiments, the mutation of the human IgG4 constant region comprises substitution of the IgG4 CH3 region with an IgG1 CH3 region, substitution of the IgG4 CH2 and CH3 regions with the IgG1 CH2 and CH3 regions or substitution of the arginine at position 409 of the IgG4 constant region (according to Kabat numbering) with a lysine, as described further in U.S. Patent Publication 20080063635. In yet other embodiments, the mutation of the human IgG4 constant region comprises substitution of Arg409, Phe405 or Lys370 (according to Kabat numbering), such as substitution of Arg409 with Lys, Ala, Thr, Met or Leu, or substitution of Phe405 with Ala, Val, Gly or Leu, as described further in PCT Publication WO 2008/145142.

A desired mutation can be introduced into the human IgG4 constant region domain using standard recombinant DNA techniques, such as site-directed mutagenesis or PCR-mediated mutagenesis of a nucleic acid encoding the human IgG4 constant region. Furthermore, DNA encoding an antibody heavy chain variable region can be introduced into an expression vector encoding a mutated human IgG4 constant region such that the variable region and constant region become operatively linked, to thereby create vector encoding a full-length immunoglobulin heavy chain in which the constant region is a mutated human IgG4 constant region. The expression vector then can be used to express the full-length immunoglobulin heavy chain using standard recombinant protein expression methods. For example, an anti-NGF antibody of the invention can be constructed as described in further detail in Example 1.

The terminal elimination half life of an antibody can be determined using standard methods known in the art. For example, after administration of the antibody to a subject (e.g., a cynomolgus monkey, a Sprague-Dawley rat), blood samples can be obtained at various time points after administration and the concentration of antibody in the serum from the blood samples can be determined using a technique known in the art for determining antibody concentration (such as an ELISA assay). Calculation of the terminal half life of the antibody can be accomplished using known pharmacokinetic methods, for example using a computer system and software designed to calculate pharmacokinetic parameters (a non-limiting example of which is the SNBL USA Pharmacokinetics Analysis System with WinNonlin software).

B. Antibody Variable Regions

Preferred antibody variable regions for use in the anti-NGF antibody of the invention are the heavy and light chain variable regions of the PG110 antibody. The heavy chain variable region of PG110 is shown in SEQ ID NO: 1 and the light chain variable region of PG110 is shown in SEQ ID NO: 2. Accordingly, in one embodiment, the anti-NGF antibody of the invention comprises a heavy chain variable region comprising the amino acid sequence of SEQ ID NO: 1. In another embodiment, the anti-NGF antibody of the invention comprises a light chain variable region comprising the amino acid sequence of SEQ ID NO: 2. In yet another embodiment, the anti-NGF antibody of the invention comprises a heavy chain variable region comprising the amino acid sequence of SEQ ID NO: 1 and a light chain variable region comprising the amino acid sequence of SEQ ID NO: 2.

The full-length amino acid sequence of the PG110 heavy chain (variable and constant regions) is shown in SEQ ID NO:

13. This heavy chain can be prepared from a precursor heavy chain, which includes a leader or signal sequence, such as the amino acid sequence shown in SEQ ID NO: 12. The precursor heavy chain of SEQ ID NO: 12 is encoded by the nucleotide sequence shown in SEQ ID NO: 11.

The full-length amino acid sequence of the PG110 light chain (variable and constant regions) is shown in SEQ ID NO: 16. This light chain can be prepared from a precursor light chain, which includes a leader or signal sequence, such as the amino acid sequence shown in SEQ ID NO: 15. The precursor light chain of SEQ ID NO: 15 is encoded by the nucleotide sequence shown in SEQ ID NO: 14.

Accordingly, in another embodiment, the invention provides an anti-NGF antibody comprising a heavy chain comprising the amino acid sequence of SEQ ID NO: 13, wherein the antibody has a serum half-life in a cynomolgus monkey of at least 15 days. In another embodiment, the serum half-life in a cynomolgus monkey can be in a range of about 15 days to about 22 days (or in a range of 15-22 days). In other embodiments, the serum half-life in a rat can be at least 8 days or in a range of about 8 days to about 9 days (or in a range of 8-9 days). In yet other embodiments, the serum half-life in a human can be at least 10-30 days, or at least 10 days, or at least 15 days, or at least 20 days, or at least 25 days, or at least 30 days or at least 40 days or in a range of about 10 days to about 40 days (or in a range of 10-40 days) or in a range of about 15 to about 30 days (or in a range of 15-30 days). Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks). Preferably, the heavy chain is encoded by the nucleotide sequence of SEQ ID NO: 11. Preferably, the light chain of the antibody comprises the amino acid sequence of SEQ ID NO: 16. Preferably, the light chain is encoded by the nucleotide sequence of SEQ ID NO: 14.

In yet another embodiment, the invention provides an anti-NGF antibody comprising a heavy chain comprising the amino acid sequence of SEQ ID NO: 13 and a light chain comprising the amino acid sequence of SEQ ID NO: 16.

In yet another embodiment, the invention provides an anti-NGF antibody comprising a heavy chain encoded by the nucleotide sequence of SEQ ID NO: 11. and a light chain encoded by the nucleotide sequence of SEQ ID NO: 14.

Given that the binding specificity of PG110 is provided by the complementarity determining regions (CDRs) of the variable domain, in another embodiment, an anti-NGF antibody of the invention comprises the CDRs of the heavy chain of PG110, the light chain of PG110 or both. The heavy chain CDRs 1, 2 and 3 of PG110 are shown in SEQ ID NOs: 3, 4 and 5, respectively. The light chain CDRs 1, 2 and 3 of PG110 are shown in SEQ ID NOs: 6, 7 and 8, respectively. Accordingly, in one embodiment, the anti-NGF antibody of the invention comprises a heavy chain variable region comprising CDRs 1, 2 and 3 having the amino acid sequences of SEQ ID NOs: 3, 4 and 5, respectively. In another embodiment, the anti-NGF antibody of the invention comprises a light chain variable region comprising CDRs 1, 2 and 3 having the amino acid sequences of SEQ ID NOs: 6, 7 and 8, respectively. In yet another embodiment, the anti-NGF antibody of the invention comprises a heavy chain variable region comprising CDRs 1, 2 and 3 having the amino acid sequences of SEQ ID NOs: 3, 4 and 5, respectively, and comprises a light chain variable region comprising CDRs 1, 2 and 3 having the amino acid sequences of SEQ ID NOs: 6, 7 and 8, respectively.

In yet another embodiment, an anti-NGF antibody of the invention can comprise heavy and light chain variable regions comprising amino acid sequences that are homologous to the heavy and/or light chain variable regions of PG110, and wherein the antibodies retain the enhanced in vivo stability exhibited by PG110. For example, the heavy chain variable region of the anti-NGF antibody can comprise an amino acid sequence that is at least 90% homologous, more preferably at least 95% homologous, more preferably at least 97% homologous and even more preferably at least 99% homologous to the amino acid sequence of SEQ ID NO: 1. The light chain variable region of the anti-NGF antibody can comprise an amino acid sequence that is at least 90% homologous, more preferably at least 95% homologous, more preferably at least 97% homologous and even more preferably at least 99% homologous to the amino acid sequence of SEQ ID NO: 2.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm. For example, the percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

In yet another embodiment, an anti-NGF antibody of the invention can comprise heavy and light chain variable regions comprising the amino acid sequences of the heavy and/or light chain variable regions of PG110 but wherein one or more conservative substitutions have been introduced into the sequence(s) yet the antibody retains the enhanced in vivo stability exhibited by PG110. For example, the heavy chain variable region of the anti-NGF antibody can comprise an amino acid sequence that is identical to the amino acid sequence of SEQ ID NO: 1 except for 1, 2, 3, 4 or 5 conservative amino acid substitutions as compared to SEQ ID NO: 1. The light chain variable region of the anti-NGF antibody can comprise an amino acid sequence that is identical to the amino acid sequence of SEQ ID NO: 2 except for 1, 2, 3, 4 or 5 conservative amino acid substitutions as compared to SEQ ID NO: 2.

As used herein, the term "conservative amino acid substitution" is intended to refer to amino acid modifications that do not significantly affect or alter the binding or stability characteristics of the antibody containing the amino acid sequence. Such conservative modifications include amino acid substitutions, additions and deletions. Modifications can be introduced into an antibody of this disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the variable regions of PG110 can be replaced with other amino acid residues from the same side chain family and the altered antibody can be tested for retained function using the functional assays described herein.

In yet another embodiment, an anti-NGF antibody of the invention comprises antigen-binding regions (i.e., variable regions) that bind to the same epitope on NGF as the PG110 antibody or that cross-compete for binding to NGF with PG110. Accordingly, in one embodiment, the anti-NGF antibody of the invention competes for binding to NGF with an antibody comprising a heavy chain variable region comprising the amino acid sequence of SEQ ID NO: 1 and a light chain variable region comprising the amino acid sequence of SEQ ID NO: 2.

Such cross-competing antibodies can be identified based on their ability to cross-compete with PG110 in standard NGF binding assays. For example, standard ELISA assays can be used in which a recombinant NGF protein (e.g., human NGF-β) is immobilized on the plate, one of the antibodies is fluorescently labeled and the ability of non-labeled antibodies to compete off the binding of the labeled antibody is evaluated. Additionally or alternatively, BIAcore analysis can be used to assess the ability of the antibodies to cross-compete. Suitable binding assays that can be used to test the ability of an antibody to compete for binding to NGF with an antibody comprising a heavy chain variable region comprising the amino acid sequence of SEQ ID NO: 1 and a light chain variable region comprising the amino acid sequence of SEQ ID NO: 2 are described in further detail in Example 2.

In still other embodiments, an anti-NGF antibody of the invention exhibits one or more functional properties of the PG110 antibody. For example, an anti-NGF antibody of the invention can exhibit one or more of the following functional properties:
 a) binds to human NGF but does not bind to human brain-derived neurotrophic factor (BDNF), human neurotrophin 3 (NT-3) or human neurotrophin 4 (NT-4);
 b) binds to human or rat NGF with a $K_D$ of 100 pM or less;
 c) inhibits binding of NGF to TrkA or $p75^{NTR}$;
 d) inhibits NGF-dependent proliferation of TF-1 cells;
 e) inhibits NGF-dependent chick dorsal root ganglion survival;
 f) inhibits NGF-dependent PC12 cell neurite outgrowth.
These functional properties can be assessed using the in vitro assays set forth in detail in Examples 2 and 3. With respect to the specific binding of the antibody to human NGF, as used herein the term "does not bind to brain-derived neurotrophic factor (BDNF), human neurotrophin 3 (NT-3) or human neurotrophin 4 (NT-4)" is intended to mean that the amount of observed binding of the antibody to BDNF, NT-3 or NT-4, in a standard binding assay (e.g., ELISA, or other suitable in vitro assay as described in the Examples) is comparable to background levels of binding (e.g., for a control antibody), for example no more than 2-fold above background levels, or less than 5% binding to BDNF, NT-3 or NT-4 as compared to binding to human NGF (wherein the level of binding to human NGF is set as 100% binding).

In yet another embodiment, the invention provides an anti-nerve growth factor (NGF) antibody comprising a human IgG4 constant region, wherein the human IgG4 constant region comprises the amino acid sequence of SEQ ID NO: 10 (or wherein the human IgG4 constant region comprises a mutation of serine at amino acid position 108 of SEQ ID NO: 9, preferably a serine to proline mutation at position 108), and wherein the antibody binds to human or rat NGF with a $K_D$ of 100 pM or less (or, alternatively, with a $K_D$ of 300 pM or less, 200 mP or less, 150 pM or less, 75 pM or less or 50 pM or less), inhibits binding of NGF to TrkA or $p75^{NTR}$ with an $IC_{50}$ of 250 pM or less (or, alternatively, with an $IC_{50}$ of 500 pM or less 400 pM or less, 300 pM or less or 200 pM or less), and inhibits NGF-dependent proliferation of TF-1 cells with an $IC_{50}$ of 50 ng/ml or less (or, alternatively, with an $IC_{50}$ of 150 ng/ml or less, 100 ng/ml or less, 75 ng/ml or less or 40 ng/ml or less). Preferably, the antibody has mean terminal elimination half-life in humans of at least 10-30 days, or at least 10 days, or at least 15 days, or at least 20 days, or at least 25 days, or at least 30 days or in a range of about 10 days to about 40 days (or in a range of 10-40 days) or in a range of about 15 days to about 30 days (or in a range of 15-30 days). Additionally or alternatively, the antibody may exhibit a mean pharmacologic half life in humans of at least 30 days, or at least 35 days, or at least 40 days, or in a range of at least four to six weeks (or in a range of four to six weeks), or in a range of at least four to seven weeks (or in a range of four to seven weeks) or in a range of at least four to eight weeks (or in a range of four to eight weeks). Additionally or alternatively, the antibody may exhibit a mean terminal elimination half life in a cynomolgus monkey of at least 15 days and typically in the range of about 15 to about 22 days (or in a range of 15-22 days), or in a range of about 15 days to about 28 days (or in a range of 15-28 days) or in a range of about 21 days to about 28 days (or in a range of 21-28 days). Additionally or alternatively, the antibody may exhibit a terminal elimination half life in rats of at least 8 days, typically in the range of about 8 to about 9 days (or in a range of 8-9 days). The antibody may further exhibit one or more additional functional properties, such as binding to human NGF but not binding to human brain-derived neurotrophic factor (BDNF), human neurotrophin 3 (NT-3) or human neurotrophin 4 (NT-4); inhibiting NGF-dependent chick dorsal root ganglion survival; and/or inhibiting NGF-dependent PC12 cell neurite outgrowth. Preferably, the antibody alleviates pain for a duration of at least about one week to about twelve weeks after administration of a single dose the anti-NGF antibody to a subject. Preferably, the antibody comprises a heavy chain variable region comprising CDRs 1, 2 and 3 having the amino acid sequences of SEQ ID NOs: 3, 4 and 5, respectively, or the antibody comprises a light chain variable region comprising CDRs 1, 2 and 3 having the amino acid sequences of SEQ ID NOs: 6, 7 and 8, respectively, or the antibody comprises a heavy chain variable region comprising CDRs 1, 2 and 3 having the amino acid sequences of SEQ ID NOs: 3, 4 and 5, respectively, and a light chain variable region comprising CDRs 1, 2 and 3 having the amino acid sequences of SEQ ID NOs: 6, 7 and 8, respectively. Preferably, the antibody comprises a heavy chain variable region comprising the amino acid sequence of SEQ ID NO: 1 or the antibody comprises a light chain variable region comprising the amino acid sequence of SEQ ID NO: 2, or the antibody comprises a heavy chain variable region comprising the amino acid sequence of SEQ ID NO: 1 and a light chain variable region comprising the amino acid sequence of SEQ ID NO: 2, or the antibody competes for binding to NGF with an antibody comprising a heavy chain variable region comprising the amino acid sequence of SEQ ID NO: 1 and a light chain variable region comprising the amino acid sequence of SEQ ID NO: 2.

In yet another embodiment, the anti-NGF antibody of the invention does not exhibit a rebound effect when administered to a subject (e.g., the antibody is administered at a dosage and at a frequency such that a rebound effect is avoided in the subject). A rebound effect, in which an anti-NGF antibody exhibits diminished efficacy in a subject after an initial period of effectiveness after single or repeat administration, has been reported in both animal models and clinical studies of other anti-NGF antibodies. For example, such an effect, referred to as a "rebound phenomenon", was reported for an anti-rat NGF antibody in a chronic constriction injury (CCI) model in rats (Ro, L-S. et al. (1999) *Pain* 79:265-274). Additionally, clinical pain studies with the anti-NGF antibody tanezumab (also known as RN624, E3, CAS Registry No. 880266-57-9) have been reported in which a period of increased adverse events, such as sensitivity to touch and a 'pins & needles' sensation, was observed after an initial analgesic period (see presentation by Hefti, Franz F., Rinat Neuroscience, LSUHSC, Shreveport, La., Sep. 26, 2006). Although not intending to be limited by mechanism, it is thought that the prolonged terminal elimination half life of the anti-NGF antibodies of the invention allows them to avoid exhibiting a rebound effect. Thus, other advantages of the anti-NGF antibodies of the invention include a more consistent and prolonged activity in vivo as compared to other prior art anti-NGF antibodies. Given the prolonged terminal elimination half life of the anti-NGF antibodies of the invention, lower dosages can be used (as compared to other anti-NGF antibodies), and the antibody can be used at more frequent intervals if necessary, such that dosage and timing treatment regimens can be chosen such that a rebound effect in the subject is avoided.

In yet another embodiment, the anti-NGF antibody of the invention is capable of alleviating pain for a long duration in a subject, for example the antibody is capable of alleviating pain for a duration of at least about one week to about twelve weeks (or for one week to twelve weeks), after administration of a single dose of the anti-NGF antibody to a subject. In one embodiment, the antibody alleviates pain for a duration of at least about one week (or at least one week) after administration of a single dose of the anti-NGF antibody to a subject. In another embodiment, the antibody alleviates pain for a duration of at least about two weeks (or at least two weeks) after administration of a single dose of the anti-NGF antibody to a subject. In another embodiment, the antibody alleviates pain for a duration of at least about four weeks (or at least four weeks) after administration of a single dose of the anti-NGF antibody to a subject. In another embodiment, the antibody alleviates pain for a duration of at least about eight weeks (or at least eight weeks) after administration of a single dose of the anti-NGF antibody to a subject. In another embodiment, the antibody alleviates pain for a duration of at least about twelve weeks (or at least twelve weeks) after administration of a single dose of the anti-NGF antibody to a subject. In another embodiment, the antibody alleviates pain for a duration of at least about four weeks to about twelve weeks (or for four weeks to twelve weeks) after administration of a single dose of the anti-NGF antibody to a subject. In another embodiment, the antibody alleviates pain for a duration of at least about eight weeks to about twelve weeks (or for eight weeks to twelve weeks) after administration of a single dose of the anti-NGF antibody to a subject.

The ability of the antibody to alleviate pain in a subject can be assessed using assays established in the art. Suitable animals models for assessing the duration of pain alleviation by an anti-NGF antibody are described in, for example, PCT Publication No. WO 2006/131951 and U.S. Patent Publication 20080182978. Non-limiting examples of such animal models include a neuropathic pain model evoked by chronic constriction of the sciatic nerve, a post-surgical pain model involving incision of the hind paw, a rheumatoid arthritis pain model involving complete Freund's adjuvant (CFA)-induced arthritis and cancer pain models such as described in Halvorson, K. G. et al. (2005) *Cancer Res.* 65:9426-9435 and Sevcik, M. A. et al. (2005) *Pain* 115:128-141. Furthermore, pain alleviation can be evaluated clinically in humans and the duration of pain alleviation can be determined based on pain levels reported by the human subject(s) being treated with the anti-NGF antibody.

In yet other embodiments, an anti-NGF antibody of the invention can comprise a heavy chain variable region and/or light chain variable region of an anti-NGF antibody described in the art. For example, a heavy chain variable region and/or light chain variable region of an anti-NGF antibody as described in PCT Publication No. WO 2001/78698, PCT Publication No. WO 2001/64247, PCT Publication No. WO 2002/096458, PCT Publication No. WO 2004/032870, PCT Publication No. WO 2004/058184, PCT Publication No. WO 2005/061540, PCT Publication No. WO 2005/019266, PCT Publication No. WO 2006/077441, PCT Publication No. WO 2006/131951, PCT Publication No. WO 2006/110883, PCT Publication No. WO 2009/023540, U.S. Pat. No. 7,449,616; U.S. Publication No. US 20050074821, U.S. Publication No. US 20080033157, U.S. Publication No. US 20080182978 or U.S. Publication No. US 20090041717 can be used in an anti-NGF antibody of the invention.

In yet other embodiments, an anti-NGF antibody of the invention can comprise a heavy chain variable region and/or light chain variable region of an anti-NGF antibody that is prepared by a standard method known in the art for raising monoclonal antibodies, such as the standard somatic cell hybridization technique described by Kohler and Milstein (1975) *Nature* 256: 495 to create non-human monoclonal antibodies (which antibodies can then be humanized), as well as phage display library techniques or methods using transgenic animals expressing human immunoglobulin genes. Phage display library techniques for selecting antibodies are described in, for example, McCafferty et al., *Nature*, 348: 552-554 (1990). Clarkson et al., *Nature*, 352:624-628 (1991), Marks et al., *J. Mol. Biol.*, 222:581-597 (1991) and Hoet et al (2005) *Nature Biotechnology* 23, 344-348; U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582, 915 and 6,593,081 to Griffiths et al. Methods of using transgenic animals expressing human immunoglobulin genes to raise antibodies are described in, for example, Lonberg, et al. (1994) *Nature* 368(6474): 856-859; Lonberg, N. and Huszar, D. (1995) *Intern. Rev. Immunol.* 13: 65-93, Harding, F. and Lonberg, N. (1995) *Ann. N.Y. Acad. Sci.* 764:536-546; U.S. Pat. Nos. 5,545,806; 5,569,825; 5,625,126; 5,633,425; 5,789, 650; 5,877,397; 5,661,016; 5,814,318; 5,874,299; and 5,770, 429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; PCT Publication WO 02/43478 to Ishida et al., U.S. Pat. Nos. 5,939,598; 6,075,181; 6,114,598; 6, 150,584 and 6,162,963 to Kucherlapati et al.

In various embodiments, an anti-NGF antibody of the invention can be a chimeric antibody, a humanized antibody or a human antibody. Furthermore, the antibody can be one in which potential T cell epitopes have been eliminated. Methods of eliminating potential T cell epitopes to thereby reduce the potential immunogenicity of an antibody have been described in the art (see e.g., U.S. Patent Publication No. 20030153043 by Carr et al.).

An antibody or antibody portion of the invention can be derivatized or linked to another functional molecule (e.g., another peptide or protein). Accordingly, the antibodies and antibody portions of the invention are intended to include derivatized and otherwise modified forms of the PG110 antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

III. ANTIBODY PRODUCTION

Another aspect of this disclosure pertains to nucleic acid molecules that encode the antibodies of this disclosure. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of this disclosure can be, for example, DNA or RNA and may or may not contain intronic sequences. In a preferred embodiment, the nucleic acid is a cDNA molecule. Nucleic acids of this disclosure can be obtained using standard molecular biology techniques.

A preferred nucleic acid molecule of the invention comprises the nucleotide sequence of SEQ ID NO: 11. Another preferred nucleic acid molecule of the invention comprises the nucleotide sequence of SEQ ID NO: 14.

Once DNA fragments encoding $V_H$ and $V_L$ segments are obtained, these DNA fragments can be further manipulated by standard recombinant DNA techniques, for example to convert the variable region genes to full-length antibody chain genes such that the variable region is operatively linked to the constant region (see e.g., Example 1). The term "operatively linked", as used in this context, is intended to mean that the two DNA fragments are joined such that the amino acid sequences encoded by the two DNA fragments remain in-frame.

Antibodies can be produced in a host cell using methods known in the art (e.g., Morrison, S. (1985) Science 229:1202). For example, to express the antibodies, the DNAs encoding the heavy and light chains can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Additionally, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of typically carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or 13-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634, 665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr– host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of this disclosure include Chinese Hamster Ovary (CHO cells) (including dhfr⁻ CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. Another preferred expression system is the GS gene expression system disclosed in WO 87/04462 (to Wilson), WO 89/01036 (to Bebbington) and EP 338,841 (to Bebbington). When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

In a preferred embodiment, the invention provides an expression vector encoding an anti-NGF antibody, wherein the vector comprises the nucleotide sequence of SEQ ID NO: 11 encoding an antibody heavy chain and the nucleotide sequence of SEQ ID NO: 14 encoding an antibody light chain. A preferred expression vector of the invention comprises the GS (glutamine synthetase) gene. In another preferred embodiment, the invention provides a host cell comprising an expression vector of the invention. A preferred host cell of the invention is a CHO (Chinese Hamster Ovary) cell. In yet another preferred embodiment, the invention provides a method of expressing an anti-NGF antibody comprising culturing a host cell comprising an expression vector comprises the nucleotide sequence of SEQ ID NO: 11 (encoding an antibody heavy chain) and the nucleotide sequence of SEQ ID NO: 14 (encoding an antibody light chain) such that an anti-NGF antibody comprising a heavy chain encoded by SEQ ID NO: 11 and a light chain encoded by SEQ ID NO: 14 is expressed.

In yet another aspect, the invention pertains to a process for making an anti-NGF antibody which has a mutation in a constant region of the antibody (e.g., a hinge region mutation), the process comprising introducing the appropriate mutation into the constant region, for example by standard recombinant DNA techniques. For example, the invention provides a process for making an anti-NGF antibody, wherein the antibody comprises (i) a heavy chain variable region comprising CDRs 1, 2 and 3 having the amino acid sequences of SEQ ID NOs: 3, 4 and 5, respectively, (ii) a light chain variable region comprising CDRs 1, 2 and 3 having the amino acid sequences of SEQ ID NOs: 6, 7 and 8, respectively, and (iii) a human IgG4 constant region, wherein the human IgG4 constant region comprises the amino acid sequence of SEQ ID NO: 10 (and, for example, wherein the antibody has a mean terminal elimination half-life in humans of at least 10-30 days, or additionally or alternatively, has a mean pharmacologic half life in humans of at least 30 days, or at least 35 days, or at least 40 days, or in a range of at least four to six weeks, or in a range of four to six weeks, or in a range of at least four to seven weeks, or in a range of four to seven weeks, or in a range of at least four to eight weeks or in a range of four to eight weeks), wherein the process for making the antibody comprises mutating the serine at amino acid position 108 of SEQ ID NO: 9 to proline to create the human IgG4 constant region comprises the amino acid sequence of SEQ ID NO: 10. Preferably, the heavy chain variable region comprises the amino acid sequence of SEQ ID NO: 1. Preferably, the light chain variable region comprises the amino acid sequence of SEQ ID NO: 2. Preferably, the heavy chain comprises the amino acid sequence of SEQ ID NO: 13. Preferably, the light chain comprises the amino acid sequence of SEQ ID NO: 16.

IV. PHARMACEUTICAL COMPOSITIONS

In another aspect, the present invention provides a composition, e.g., a pharmaceutical composition, containing an antibody of the invention formulated together with a pharmaceutically acceptable carrier. In preferred embodiments, the pharmaceutical composition is suitable for administration intravenously, subcutaneously (e.g., via an injection pen) or intra-articularly, although other suitable routes of administration are described herein. In one embodiment, the composition can include a combination of multiple (e.g., two or more) antibodies of the invention, for example, antibodies that bind different epitopes on NGF.

As used herein, "pharmaceutically acceptable carrier" includes any and all solvents, salts, dispersion media, coatings, antibacterial and antifungal agents, isotonic and absorption delaying agents, and the like that are physiologically compatible. Depending on the route of administration, the active compound may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutical compositions of the invention can be administered alone or in combination therapy, i.e., combined with other agents. For example, the combination therapy can include a composition of the present invention with at least one or more additional pharmaceutical agents. For example, at least one or more additional pharmaceutical agents may be administered separately or can also be incorporated into the compositions. In a preferred embodiment, an anti-NGF antibody of the invention is administered in combination with a second pharmaceutical agent, wherein the second pharmaceutical agent is selected from the group consisting of NSAIDs, analgesics (including opioid analgesics and atypical analgesics), local anaesthetics, nerve blocks, phenol blocks, therapeutic antibodies, steroids, anti-convulsants, anti-depressants, topical capsaicin and antiviral agents. A particularly preferred class of second pharmaceutical agents for use in pain alleviation are the opioid analgesics. Additionally or alternatively, a second treatment regimen can be combined with use of an antibody of the invention, for example in the alleviation of pain. Examples of such second treatment regimens include radiotherapy (e.g., for cancer pain), surgical procedures (e.g., gasserian ganglion and retrogasserian ablative (needle) procedures for trigeminal neuralgia), hypnosis and acupuncture.

Examples of NSAIDS include acetylated salicylates including aspirin; nonacetylated salicylates including salsalate, diflunisal; acetic acids including etodolac, diclofenac, indomethacin, ketorolac, nabumetone; propionic acids including fenoprofen, flurbiprofen, ibuprofen, ketoprofen, naproxen, naproxen sodium, oxaprozin; fenamates including meclofenamate, mefenamic acid; phenylbutazone, piroxicam; COX-2 inhibitors including celecoxib, etoricoxib, valdecoxib, rofecoxib, lumiracoxib. Examples of analgesics include paracetamol (acetaminophen), tramadol, tapentadol, capsaicin (topical), opioid analgesics and atypical analgesics. Examples of opioid analgesics include morphine, codeine, thebaine, hydromorphone, hydrocodone, oxycodone, oxymorphone, desomorphine, diacetylmorphine, nicomorphine, dipropanoylmorphine, benzylmorphine, ethylmorphine, fentanyl, pethidine, methadone, tramadol and propoxyphene. Examples of atypical analgesics include trycyclic anti-depressants, carbazepine, gabapentin, pregabalin, duloxetine and caffeine. Examples of steroids include intraarticular corticosteroids (IACs) and prednisone. Examples of therapeutic antibodies include anti-TNF antibodies, such as Remicade® and Humira®, and antiCD20 antibodies, such as Rituxan® and Arzerra™. Examples of antiviral agents include acyclovir and oseltamivir phosphate (Tamiflu®).

In a preferred embodiment, the combination therapy can include an anti-NGF antibody of the present invention with at least one or more TrkA inhibitors (e.g., compounds that antagonize TrkA activity). TrkA inhibitors can function, for example, by interacting extracellularly with the TrkA receptor, or by interacting intracellularly with the TrkA signaling transduction machinery (e.g., inhibition of TrkA kinase activity). Non-limiting examples of extracellular TrkA inhibitors include anti-TrkA antibodies (such as the humanized anti-TrkA antibodies described in US Patent Publication No. 20090208490 and US Patent Publication No. 20090300780) and NGF peptide mimetics that antagonize TrkA (such as described in Debeir, T. et al. (1999) *Proc. Natl. Acad. Sci. USA* 96:4067-4072). Non-limiting examples of intracellular TrkA inhibitors include cell-penetrating peptides that antagonize TrkA function (e.g., as described in Hirose, M. et al. (2008) *J. Pharmacol. Sci.* 106:107-113; Ueda, K. et al. (2010) *J. Pharmacol. Sci., Mar.* 30, 2010 issue) and small molecule inhibitors such as TrkA kinase inhibitors (e.g., as described in Wood, E. R. et al. (2004) *Bioorg. Med. Chem. Lett.* 14:953-957; Tripathy, R. et al. (2008) *Bioorg. Med. Chem. Lett.* 18:3551-3555). Other non-limiting examples of TrkA inhibitors include ARRY-470 and ARRY-872 (Array Biopharma).

In another preferred embodiment, the combination therapy can include an anti-NGF antibody of the present invention with at least one or more Protein Kinase C (PKC) inhibitors (e.g., compounds that antagonize PKC activity).

A composition of the present invention can be administered by a variety of methods known in the art. As will be appreciated by the skilled artisan, the route and/or mode of administration will vary depending upon the desired results. Preferably, the carrier is suitable for intravenous, intra-articular, subcutaneous, intramuscular, parenteral, intra-tumoral, intranasal, intravesicular, intrasynovial, oral, mucosal, sublingual, spinal or epidermal administration or by instillation into body cavities (e.g., abdomen, pleural cavity, nasal sinuses) or onto the surface of the eye, or into the lungs by administration by inhalation. For particular routes of administration, a suitable delivery device may be chosen for use. For example, for subcutaneous or intramuscular administration, an injection pen (e.g., that can be self-administered) can be used. Such injection pens, also referred to as injectors, are known in the art, including those that contain a liquid dose of antibody (such as the single-use injection pen used to administer Humira®) and, more preferably, those that contain a solid dose of antibody that is reconstituted into a liquid form immediately prior to injection. Also for subcutaneous administration, a subcutaneous implant can be used. Additionally, transcutaneous delivery can be achieved by use of a topical cutaneous (skin) patch (e.g., adhesive patch). Transcutaneous delivery also can be achieved by injection of dry powder (such as injectors commercially available from Glide Pharma). Still further, for delivery into the lungs (e.g., in the treatment of asthma or intractable cough), a nebulized solution in a nebulizing device can be used.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. A typical single dose (which may be administered on a dosing schedule as described further below) might range from about any of 0.1 μg/kg to 1 μg/kg to 3 μg/kg to 30 μg/kg to 300 μg/kg to 3000 μg/kg (3 mg/kg), to 30 mg/kg to 100 mg/kg or more, depending on the factors described herein. For example, an anti-NGF antibody may be administered at about 1 μg/kg, about 10 μg/kg, about 20 μg/kg, about 50 μg/kg, about 100 μg/kg, about 200 μg/kg, about 300 μg/kg, about 400 μg/kg about 500 μg/kg, about 1 mg/kg, about 2 mg/kg or about 3 mg/kg. In a preferred embodiment, the anti-NGF antibody is administered at a dose in a range from about 3 μg/kg to about 3000 μg/kg. In another preferred embodiment, the anti-NGF antibody is administered at a dose of 100 μg/kg. In another preferred embodiment, the anti-NGF antibody is administered at a dose of 200 μg/kg. In another preferred embodiment, the anti-NGF antibody is administered at a dose of 300 μg/kg. In another preferred embodiment, the anti-NGF antibody is administered at a dose of 400 μg/kg.

For repeated administrations over several days, weeks or months or longer, depending on the condition, the treatment is sustained until a desired suppression of symptoms occurs or until sufficient therapeutic levels are achieved (e.g., to reduce pain). An exemplary dosing regimen comprises administering an initial dose in a range of about 3 μg/kg to 500 μg/kg, followed by a monthly maintenance dose of about 3 μg/kg to 500 μg/kg of the anti-NGF antibody. In another embodiment, a dose of about 200 μg/kg is administered once every month. In yet another embodiment, a dose of about 400 μg/kg is administered once every two months. However, other dosage regimens may be useful, depending on the pattern of pharmacokinetic decay that the practitioner wishes to achieve. For example, in some embodiments, dosing from one to four times a week is contemplated. However, given the long duration of pain alleviation by the anti-NGF antibodies, less frequent dosing may be used. In some embodiments, the anti-NGF antibody is administered once every week, once every 2 weeks, once every 3 weeks, once every 4 weeks, once every 5 weeks, once every 6 weeks, once every 7 weeks, once every 8 weeks, once every 9 weeks, once every 10 weeks, once every 15 weeks, once every 20 weeks, once every 25 weeks, once every 26 weeks, or longer. In some embodiments, the anti-NGF antibody is administered once every 1 month, once every 2 months, once every 3 months, once every 4 months, once every 5 months, once every 6 months, or longer.

As discussed further in Example 6, in a preferred embodiment, an anti-NGF antibody of the invention is administered (e.g., to a human) intravenously at a dose in a range of 0.1 mg/kg to 0.2 mg/kg, preferably 0.15 mg/kg, once every 12 weeks. In another preferred embodiment, an anti-NGF antibody of the invention is administered (e.g., to a human) subcutaneously at a dose in a range of 0.2 mg/kg to 0.4 mg/kg, preferably 0.3 mg/kg, once every twelve weeks. In yet other embodiments, an anti-NGF antibody of the invention is administered at a dose in a range of 0.1 mg/kg to 3 mg/kg, or in a range of 0.1 mg/kg to 30 mg/kg, or in a range of 0.1 mg/kg to 20 mg/kg, or in a range of 0.1 mg/kg to 10 mg/kg, or in a range of 1 mg/kg to 30 mg/kg, or in a range of 1 mg/kg to 20 mg/kg or in a range of 1 mg/kg to 10 mg/kg.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals. For example, non-limiting examples of dosage unit forms include 0.2 mg (corresponding to a dose of 3 μg/kg in a person of about 70 kg), 2 mg (corresponding to a dose of 30 μg/kg in a person of about 70 kg) and 7 mg (corresponding to a dose of 100 μg/kg in a person of about 70 kg).

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations may conveniently be presented in dosage unit form and may be prepared by any methods known in the art of pharmacy. Dosage unit form as used herein refers to physically discrete units suited as unitary dosages for the subjects to be treated; each unit containing a predetermined quantity of active compound calculated to produce the desired therapeutic effect in association with the required pharmaceutical carrier. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Particular examples of adjuvants which are well-known in the art include, for example, inorganic adjuvants (such as aluminum salts, e.g., aluminum phosphate and aluminumhydroxide), organic adjuvants (e.g., squalene), oil-based adjuvants, virosomes (e.g., virosomes which contain a membrane-bound hemagglutinin and neuraminidase derived from the influenza virus).

Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above.

Therapeutic compositions can be administered with medical devices known in the art. For example, in a preferred embodiment, a therapeutic composition of the invention can be administered with a needleless hypodermic injection device, such as the devices disclosed in U.S. Pat. No. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimi-* crob. *Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

V. METHODS OF USING ANTIBODIES OF THE INVENTION

In another aspect, the invention provides a method of treating, e.g., attenuating or inhibiting, an NGF-related disease or condition in a subject, the method comprising administering to the subject the anti-NGF antibody of the invention. Preferably, the anti-NGF antibody is used to attenuate or alleviate pain, e.g., pain associated with a disease or condition wherein the development or maintenance of the pain is mediated, at least in part, by NGF. Non-limiting examples of NGF-related disease or condition include inflammatory pain, post-surgical pain, post-operative pain (including dental pain), neuropathic pain, peripheral neuropathy, diabetic neuropathy, fracture pain, gout joint pain, post-herpetic neuralgia, cancer pain, osteoarthritis or rheumatoid arthritis pain, sciatica, pains associated with sickle cell crises, headaches (e.g., migraines, tension headache, cluster headache), dysmenorrhea, endometriosis, uterine fibroids, musculoskeletal pain, chronic low back pain, fibromyalgia, sprains, visceral pain, ovarian cysts, prostatitis, chronic pelvic pain syndrome, cystitis, interstitial cystitis, painful bladder syndrome and/or bladder pain syndrome, pain associated with chronic abacterial prostatitis, incisional pain, migraine, trigeminal neuralgia, pain from burns and/or wounds, pain associated with trauma, pain associated with musculoskeletal diseases, ankylosing spondilitis, periarticular pathologies, pain from bone metastases, pain from HIV, erythromelalgia or pain caused by pancreatitis or kidney stones, malignant melanoma, Sjogren's syndrome, asthma, (e.g., uncontrolled asthma with severe airway hyper-responsiveness), intractable cough, demyelinating diseases, chronic alcoholism, stroke, thalamic pain syndrome, pain from toxins, pain from chemotherapy, fibromyalgia, inflammatory bowel disorders, irritable bowel syndrome, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia or allodynia, diabetic neuropathy pain, causalgia, sympathetically maintained pain, deafferentation syndromes, epithelial tissue damage or dysfunction, disturbances of visceral motility at respiratory, genitourinary, gastrointestinal or vascular regions, allergic skin reactions, pruritis, vitiligo, general gastrointestinal disorders, colitis, gastric ulceration, duodenal ulcers, vasomotor or allergic rhinitis, bronchial disorders, dyspepsia, gastroesophageal reflux, pancreatitis, and visceralgia.

Furthermore, NGF has been implicated in the proliferation of cancers such as prostate cancer, thyroid cancer, lung cancer, prolactinoma and melanoma. Accordingly, in another embodiment, the NGF-related disease or condition that can be treated using an anti-NGF antibody of the invention is cancer, preferably prostate cancer, thyroid cancer, lung cancer, prolactinoma or melanoma. Thus, in another embodiment, the invention also provides a method of treating cancer in a subject, preferably prostate cancer, thyroid cancer, lung cancer, prolactinoma or melanoma, comprising administering an anti-NGF antibody of the invention to the subject.

Still further, in another embodiment, the NGF-related disease or condition can be HIV/AIDS. Blockage of NGF using an anti-NGF antibody of the invention may block HIV infected macrophages, thereby treating HIV/AIDS. Accordingly, in another embodiment, the invention also provides a method of treating HIV/AIDS in a subject, comprising administering an anti-NGF antibody of the invention to the subject.

Particularly preferred diseases and conditions for treatment according to the methods of the invention include inflammatory pain (particularly osteoarthritis or rheumatoid arthritis pain), musculoskeletal pain (particularly chronic low back pain), cancer pain, neuropathic pain (particularly diabetic neuropathic pain), pain from bone metastases, interstitial cystitis/painful bladder syndrome, pain associated with chronic abacterial prostatitis, pain from endometriosis and/or uterine fibroids, and post-operative pain.

Pain and/or other symptoms associated with endometriosis and/or uterine fibroids may comprise dysmenorrhoea; chronic non-menstrual, pelvic pain; dyspareunia; dyschexia; menorrhagia; lower abdominal or back pain; infertility and subfertility; dysuria; bloating and pain on micturition; nausea, vomiting and/or diarrohea. Symptoms may also comprise symptoms related to endometriotic lesions or fibroids located outside the peritoneal cavity including for example thoracic endometriosis syndrome manifest as haemoptysis, pneumothorax or haemothorax, and pulmonary leiomyosis manifest as dyspnoea and a pulmonary mass.

In a particularly preferred embodiment, an anti-NGF antibody of the invention is used to treat pain. Preferably, the type of pain treated is selected from the group consisting of osteoarthritis pain, chronic low back pain, diabetic neuropathic pain, cancer pain and endometriosis and/or uterine fibroid pain. Accordingly, in a preferred embodiment, the invention provides a method of treating pain in a subject comprising administering an anti-NGF antibody of the invention such that pain in the subject is treated. Preferably, the pain is selected from the group consisting of osteoarthritis pain, chronic low back pain, diabetic neuropathic pain, cancer pain and endometriosis and/or uterine fibroid pain. Accordingly, in one embodiment, the invention provides a method of treating osteoarthritis pain in a subject comprising administering an anti-NGF antibody of the invention such that osteoarthritis pain in the subject is treated. In another embodiment, the invention provides a method of treating chronic low back pain in a subject comprising administering an anti-NGF antibody of the invention such that chronic low back pain in the subject is treated. In yet another embodiment, the invention provides a method of treating diabetic neuropathic pain in a subject comprising administering an anti-NGF antibody of the invention such that diabetic neuropathic pain in the subject is treated. In yet another embodiment, the invention provides a method of treating cancer pain in a subject comprising administering an anti-NGF antibody of the invention such that cancer pain in the subject is treated. In yet another embodiment, the invention provides a method of treating endometriosis and/or uterine fibroid pain in a subject comprising administering an anti-NGF antibody of the invention such that endometriosis and/or uterine fibroid pain in the subject is treated.

In another embodiment, the invention provides an anti-NGF antibody as described herein for treating an NGF-related disease. Non-limiting examples of NGF-related diseases or conditions include those listed above. In another embodiment, the invention provides an anti-NGF antibody as described herein for treating pain. In yet another embodiment, the invention provides an anti-NGF antibody as described herein for treating pain selected from the group consisting of osteoarthritis pain, chronic low back pain, diabetic neuropathic pain, cancer pain and endometriosis and/or uterine fibroid pain. In yet another embodiment, the invention provides an anti-NGF antibody as described herein for treating osteoarthritis pain. In yet another embodiment, the invention provides an anti-NGF antibody as described herein for treating chronic low back pain. In yet another embodiment, the invention provides an anti-NGF antibody as described herein for treating diabetic neuropathic pain. In yet another embodiment, the invention provides an anti-NGF antibody as described herein for treating cancer pain. In yet another embodiment, the invention provides an anti-NGF antibody as described herein for treating endometriosis and/or uterine fibroid pain.

In a particular embodiment, the invention provides a method of attenuating or inhibiting pain in a subject, the method comprising administering to the subject an anti-nerve growth factor (NGF) antibody comprising a human IgG4 constant region, wherein the human IgG4 constant region comprises the amino acid sequence of SEQ ID NO: 10, and wherein the antibody alleviates pain in the subject for a duration of at least about four weeks to about twelve weeks (or at least four to twelve weeks, or at least four weeks, or at least eight weeks, or at least twelve weeks, or for one to twelve weeks, or for four to twelve weeks or for eight to twelve weeks) after administration of a single dose of the anti-NGF antibody to a subject. Preferably, the pain is selected from the group consisting of osteoarthritis pain, chronic low back pain, diabetic neuropathic pain, cancer pain, endometriosis pain and uterine fibroid pain. Preferably the anti-NGF antibody is administered at a dose in a range from about 0.1 mg/kg to 3 mg/kg, or from 0.1 mg/kg to 3 mg/kg, or from about 0.1 mg/kg to about 30 mg/kg, or from 0.1 mg/kg to 30 mg/kg or at one of the other dosage ranges described herein.

In another particular embodiment, the invention provides a method of attenuating or inhibiting a nerve growth factor (NGF)-related disease or condition in a subject such that a rebound effect is avoided in the subject, the method comprising administering to the subject an anti-NGF antibody comprising a human IgG4 constant region, wherein the human IgG4 constant region comprises a hinge region mutation at amino acid position 108 of SEQ ID NO: 9, and wherein the antibody has a terminal elimination half-life in a human of at least 10-30 days (or at least 10 days, or at least 15 days, or at least 20 days, or at least 25 days, or at least 30 days, or at least 40 days, or in a range of about 10 days to about 40 days, or in a range of 10-40 days, or in a range of about 15 to about 30 days, or in a range of 15-30 days), wherein the antibody is administered to the subject at a dosage and at a frequency such that a rebound effect is avoided in the subject. Preferably, the serine at amino acid position 108 of SEQ ID NO: 9 is mutated to proline. Preferably, the human IgG4 constant region comprises the amino acid sequence of SEQ ID NO: 10. Preferably, the antibody competes for binding to NGF with an antibody comprising a heavy chain variable region comprising the amino acid sequence of SEQ ID NO: 1 and a light chain variable region comprising the amino acid sequence of SEQ ID NO: 2. Preferably, the NGF-related disease or condition is pain selected from the group consisting of osteoarthritis pain, chronic low back pain, diabetic neuropathic pain, cancer pain, endometriosis pain and uterine fibroid pain. Preferably, the anti-NGF antibody is administered at a dose in a range from about 0.001 mg/kg to about 30 mg/kg, more preferably from 0.1 mg/kg to 3 mg/kg, or at one of the other dosage ranges described herein. More preferably, to avoid a rebound effect, the antibody is administered at a lower dosage range, for example in a range of 0.001 mg/kg to 1 mg/kg, or in a range of 0.001 mg/kg to 1 mg/kg or in a range of 0.001 mg/kg to 0.5 mg/kg or in a range of 0.001 mg/kg to 0.3 mg/kg, or in a range of 0.01 mg/kg to 1 mg/kg or in a range of 0.01 mg/kg to 0.5 mg/kg or 0.01 mg/kg to 0.3 mg/kg. More preferably, to avoid a rebound effect, the antibody is administered at a lower dosage range (as set forth above) and at more frequent intervals, such as once every week, or once every two weeks, or once every four weeks.

The invention also provides for use of the anti-NGF antibody of the invention for the manufacture of a medicament for use to attenuate or inhibit an NGF-related disease or condition in a subject. Non-limiting examples of NGF-related diseases or conditions include those listed above. In another embodiment, the invention provides an anti-NGF antibody of the invention for the manufacture of a medicament for the treatment of pain. In yet another embodiment, the invention provides an anti-NGF antibody of the invention for the manufacture of a medicament for treating pain selected from the group consisting of osteoarthritis pain, chronic low back pain, diabetic neuropathic pain, cancer pain and endometriosis and/or uterine fibroid pain. In yet another embodiment, the invention provides an anti-NGF antibody of the invention for the manufacture of a medicament for the treatment of osteoarthritis pain. In yet another embodiment, the invention provides an anti-NGF antibody of the invention for the manufacture of a medicament for the treatment of chronic low back pain. In yet another embodiment, the invention provides an anti-NGF antibody of the invention for the manufacture of a medicament for the treatment of diabetic neuropathic pain. In yet another embodiment, the invention provides an anti-NGF antibody of the invention for the manufacture of a medicament for the treatment of cancer pain. In yet another embodiment, the invention provides an anti-NGF antibody of the invention for the manufacture of a medicament for the treatment of endometriosis and/or uterine fibroid pain. In a preferred embodiment, the anti-NGF antibody is administered at a dose in a range from about 3 µg/kg to about 3000 µg/kg, or at a dose of 100 µg/kg, or at a dose of 300 µg/kg. In another preferred embodiment, an anti-NGF antibody of the invention is administered (e.g., to a human) intravenously at a dose in a range of 0.1 mg/kg to 0.2 mg/kg, preferably 0.15 mg/kg, once every 12 weeks. In another preferred embodiment, an anti-NGF antibody of the invention is administered (e.g., to a human) subcutaneously at a dose in a range of 0.2 mg/kg to 0.4 mg/kg, preferably 0.3 mg/kg, once every twelve weeks. In yet other embodiments, an anti-NGF antibody of the invention is administered at a dose in a range of 0.1 mg/kg to 3 mg/kg, or in a range of 0.1 mg/kg to 30 mg/kg, or in a range of 0.1 mg/kg to 20 mg/kg, or in a range of 0.1 mg/kg to 10 mg/kg, or in a range of 1 mg/kg to 30 mg/kg, or in a range of 1 mg/kg to 20 mg/kg or in a range of 1 mg/kg to 10 mg/kg. However, other suitable dosage ranges and doses are set forth above in the section on pharmaceutical compositions.

In a preferred embodiment, the anti-NGF antibody is administered intravenously. In another preferred embodiment, the anti-NGF antibody is administered subcutaneously or intra-articularly. However, other suitable routes of administration are set forth above in the section on pharmaceutical compositions.

In a preferred embodiment, an anti-NGF antibody of the invention alleviates pain in a subject to which the antibody is administered for a long duration. For example, in one embodiment, the antibody alleviates pain for a duration of at least about one week to about twelve weeks (or for at least one week to twelve weeks) after administration of a single dose of the anti-NGF antibody to a subject. In another embodiment, the antibody alleviates pain for a duration of at least about one week (or at least one week) after administration of a single dose of the anti-NGF antibody to a subject. In another embodiment, the antibody alleviates pain for a duration of at least about two weeks (or at least two weeks) after administration of a single dose of the anti-NGF antibody to a subject. In another embodiment, the antibody alleviates pain for a duration of at least about four weeks (or at least four weeks) after administration of a single dose of the anti-NGF antibody to a subject. In another embodiment, the antibody alleviates pain for a duration of at least about eight weeks (or at least eight weeks) after administration of a single dose of the anti-NGF antibody to a subject. In another embodiment, the antibody alleviates pain for a duration of at least about twelve weeks (or at least twelve weeks) after administration of a single dose of the anti-NGF antibody to a subject. In one embodiment, the antibody alleviates pain for a duration of at least about four weeks to about twelve weeks (or for four weeks to twelve weeks) after administration of a single dose of the anti-NGF antibody to a subject. In one embodiment, the antibody alleviates pain for a duration of at least about eight weeks to about twelve weeks (or for eight weeks to twelve weeks) after administration of a single dose of the anti-NGF antibody to a subject.

In another embodiment, the anti-NGF antibody is administered together with a second pharmaceutical agent or a second treatment regimen. The antibody and the second agent, or the antibody and the second treatment regimen, can be administered or performed simultaneously or, alternatively, the antibody can be administered first, followed by the second pharmaceutical agent or second regimen, or the second pharmaceutical agent or regimen can be administered or performed first, followed by the antibody. Non-limiting examples of suitable second pharmaceutical agents and second treatment regimens are set forth above in the section on pharmaceutical compositions. Particularly referred second pharmaceutical agents for use in combination with an antibody of the invention are opioid analgesics. Other preferred second pharmaceutical agents for use in combination with an antibody of the invention are TrkA inhibitors (e.g., extracellular TrkA inhibitors or intracellular TrkA inhibitors, as described in detail in the section on pharmaceutical compositions) and Protein Kinase C (PKC) inhibitors.

In yet another aspect, the invention provides a method of attenuating or inhibiting a nerve growth factor (NGF)-related disease or condition in a subject such that a rebound effect is avoided in the subject, the method comprising administering to the subject an anti-NGF antibody of the invention, such as an anti-NGF antibody comprising a human IgG4 constant region, wherein the human IgG4 constant region comprises a mutation (preferably a hinge region mutation) and wherein the antibody has a terminal elimination half-life in a cynomolgus monkey of at least 15 days. In another embodiment, the antibody has a terminal elimination half-life in a cynomolgus monkey in a range of about 15 days to about 22 days (or in a range of 15-22 days), or in a range of about 15 days to about 28 days (or in a range of 15-28 days), or in a range of about 21 days to about 28 days (or in a range of 21-28 days). In another embodiment, the antibody has a terminal elimination half-life in a rat of at least 8 days. In yet another embodiment, the antibody has a mean terminal elimination half-life in humans of at least 10-30 days (or at least 10 days, at least 15 days, at least 20 days, at least 25 days, at least 30 days, at least 40 days, or in a range of about 10 days to about 40 days or in a range of 10-40 days or in a range of about 15 to about 30 days or in a range of 15-30 days). Preferred mutations include those described in detail hereinbefore. Preferred antibodies include anti-NGF antibodies of the sequences and/or having the functional properties described in detail hereinbefore. Non-limiting examples of NGF-related diseases or conditions include those described in detail hereinbefore. The invention also provides for use of an anti-NGF antibody of the invention for the manufacture of a medicament for use to attenuate or inhibit an NGF-related disease or condition in a subject such that a rebound effect is avoided in the subject (e.g., the antibody is administered at a dosage and at a frequency such that a rebound effect is avoided in the subject).

VI. ARTICLES OF MANUFACTURE

Also within the scope of the present invention are kits comprising antibodies of the invention which optionally include instructions for use in treating an NGF-related disease or condition The kits may include a label indicating the intended use of the contents of the kit. The term label includes any writing, marketing materials or recorded material supplied on or with the kit, or which otherwise accompanies the kit.

For example, the invention also provides a packaged pharmaceutical composition wherein the PG110 antibody (having a heavy chain as shown in SEQ ID NO: 13 and having a light chain as shown in SEQ ID NO: 16), or derivatized forms, as described herein, is packaged within a kit or an article of manufacture. The kit or article of manufacture of the invention contains materials useful for the treatment, including prevention, treatment and/or diagnosis of an NGF related disease or condition in a subject. In preferred embodiments, the NGF related disease or condition is inflammatory pain (particularly osteoarthritis or rheumatoid arthritis pain), musculoskeletal pain (particularly chronic low back pain), neuropathic pain (particularly diabetic neuropathic pain), cancer pain (particularly pain from bone metastases), pain associated with endometriosis and/or uterine fibroids, and postoperative pain. The kit or article of manufacture comprises a container and a label or package insert or printed material on or associated with the container which provides information regarding use of the PG110 antibody, for the treatment of an NGF related disease or condition described herein.

A kit or an article of manufacture refers to a packaged product comprising components with which to administer a PG110 antibody for treatment of an NGF related disease or condition. The kit preferably comprises a box or container that holds the components of the kit, and can also include a protocol for administering the PG110 antibody and/or a "package insert". The box or container holds components of the invention which are preferably contained within plastic, polyethylene, polypropylene, ethylene, or propylene vessels. For example, suitable containers for the PG110 antibody, include, for example, bottles, vials, syringes, pens, etc.

The term "package insert" is used to refer to instructions customarily included in commercial packages of therapeutic products, that contain information about the indications, usage, dosage, administration, contraindications and/or warnings concerning the use of such therapeutic products. In one embodiment, the package insert of the invention informs a reader, including a subject, e.g., a purchaser, who will be administering the PG110 for treatment, that the PG110 antibody is indicated for treatment of an NGF related disease or condition as described herein. In one embodiment, the package insert describes certain therapeutic benefits of the PG110 antibody, including alleviation of pain. In another embodiment, the package insert can include a description of the dosage of the PG110 antibody. In another embodiment, the package insert can include a description of the route and frequency of administration of the PG110 antibody. In another embodiment, the package insert of the invention may also provide information to subjects who will be receiving PG110 antibody regarding combination uses for both safety and efficacy purposes. For example, in certain embodiments the kit further comprises a second pharmaceutical composition comprising an additional therapeutic packaged with or copromoted with instructions for administration of both agents for the treatment of an NGF-related disease or condition. Particularly preferred diseases and conditions for treatment using the kits of the invention include inflammatory pain (particularly osteoarthritis or rheumatoid arthritis pain), musculoskeletal pain (particularly chronic low back pain), neuropathic pain (particularly diabetic neuropathy), cancer pain and pain from bone metastases, pain associated with endometriosis and/or uterine fibroids, and post-operative pain.

Other embodiments of the present invention are described in the following Examples.

The present invention is further illustrated by the following examples which should not be construed as further limiting. The contents of Sequence Listings, figures and all references, patents and published patent applications cited throughout this application are expressly incorporated herein by reference.

EXAMPLES

Example 1

Construction of an Anti-NGF Antibody, PG110, with a Mutated IgG4 Hinge Region

In this example, a mutated form of a humanized anti-NGF antibody was created by introducing a Serine to Proline mutation in the hinge region of the IgG4 constant region.

The heavy chain variable region and light chain variable region of the humanized anti-NGF antibody alphaD11 were used. The humanized alphaD11 antibody is described in further detail in PCT Publications WO 2005/061540 and WO 2006/131951. The amino acid sequence of the heavy chain variable region of alphaD11 (Hu-alphaD11 $V_H$) is shown in SEQ ID NO: 1. The amino acid sequence of the light chain variable region of alphaD11 (Hu-alphaD11 $V_L$) is shown in SEQ ID NO: 2. The CDR1, 2 and 3 regions of Hu-alphaD11 $V_H$ are shown in SEQ ID NOs: 3, 4 and 5, respectively. The CDR1, 2 and 3 regions of Hu-alphaD11 $V_L$ are shown in SEQ ID NOs: 6, 7 and 8, respectively.

Nucleic acid sequence encoding Hu-alphaD11 $V_H$ was joined at the 3' end to Lonza Biologic's IgG4-Pro constant region (which encodes a mutation that alters amino acid residue 108 of the constant sequence from a serine to a proline). A murine IgG1 derived signal sequence was introduced at the 5' end to produce the complete Hu-alphaD11 heavy chain cDNA sequence. The amino acid sequence of the wild type human IgG4 constant region is shown in SEQ ID NO: 9, whereas the amino acid sequence of the mutated human IgG4 constant region is shown in SEQ ID NO: 10. Within SEQ ID NOs: 9 and 10, the amino acid that is mutated from serine (in SEQ ID NO: 9) to proline (in SEQ ID NO: 10) is located at amino acid position 108.

Nucleic acid sequence encoding Hu-alphaD11 $V_L$ was linked at the 3' end to the human kappa constant region (supplied by Lonza Biologics) and a murine IgG1 derived signal sequence introduced at the 5' to thereby encode a full-length light chain variable region.

Since the antibody was to be expressed in Chinese Hamster Ovary (CHO cells) codon optimization was performed (Geneart; using GeneOptimizer™ software) that involved adaptation of the antibody sequences to the codon bias of *Cricetulus griseus* (Chinese hamster) genes. Additionally, regions of very high (>80%) or very low (<30%) GC-content were avoided where possible. During the optimization process, the following cis-acting sequence motifs were avoided: internal TATA-boxes, chi-sites and ribosomal entry sites; AT-rich or GC-rich sequence stretches; ARE, INS, CRS sequence elements (involved in vector replication in bacteria); repeat sequences and RNA secondary structures; (cryptic) splice donor and acceptor sites and branch points; specified internal restriction enzyme sites (Eco RI, Hind III, Pvu I and Not I). Antibody gene sequence optimization, including codon optimization, and expression of antibody genes in CHO cells is described in further detail in PCT Application WO 2006/122822, owned by Lonza Biologics PLC.

The optimized heavy and light chain variable region sequences (including the signal sequences) were cloned into the GS vectors pEE6.4 and pEE12.4, respectively (supplied by Lonza Biologics) to generate two single gene vectors (SGVs). Then, a double gene vector (DGV) was constructed by ligating the complete expression cassette from the heavy chain vector into the light chain vector, to create a single vector expressing both complete heavy and light chain genes, as well as the GS (glutamine synthetase) gene.

The resultant mutant antibody was referred to as PG110. The nucleotide sequence of the complete PG110 heavy chain (including signal sequence, variable region and mutated IgG4 constant region) is shown in SEQ ID NO: 11. The amino acid sequence of the complete PG110 heavy chain (including signal sequence, variable region and mutated IgG4 constant region) is shown in SEQ ID NO: 12, wherein amino acid residues 1-19 constitute the signal sequence and amino acids 20-141 constitute the variable region. The amino acid sequence of the mature PG110 heavy chain, without signal sequence (including the variable region and mutated IgG4 constant region) is shown in SEQ ID NO: 13.

The nucleotide sequence of the complete PG110 light chain (including signal sequence, variable region and kappa constant region) is shown in SEQ ID NO: 14. The amino acid sequence of the complete PG110 light chain (including signal sequence, variable region and kappa constant region) is shown in SEQ ID NO: 15, wherein amino acid residues 1-20 constitute the signal sequence and amino acids 21-127 constitute the variable region. The amino acid sequence of the mature PG110 light chain, without signal sequence (including the variable region and kappa constant region) is shown in SEQ ID NO: 16.

To verify expression of the PG110 antibody, the DGV encoding the heavy and light chains of PG110 was transiently transfected into CHOK1SV cells (supplied by Lonza Biologics). Cells ($0.125 \times 10^6$ viable cells per well) were plated into 24-well plates in a DMEM-based medium supplemented with 10% fetal bovine serum and 6 mM L-glutamine, and incubated overnight at 37° C. (10% $CO_2$ incubator). Prior to transfection, the seeding medium was replaced with 800 μl fresh medium and cells were incubated for 1 hour at 37° C.

For each transfection, 5 μg of the PG110 DGV was resuspended in 100 μl transfection medium (OptiMEM, Invitrogen). A vector encoding another IgG$_4$/kappa antibody was used as a positive control and buffer only was used as a negative control. For each transfection, 5 μl of Lipofectamine-2000 reagent (Invitrogen) was diluted in 100 μl transfection medium. After a 5 minute incubation at room temperature, the DNA and diluted Lipofectamine reagent were combined, mixed and left to stand at ambient temperature for 20 minutes. This 205 µl mixture was then added to a well of the 24-well plate containing cells. Cells were incubated for 68-72 hours at 37° C. The culture supernatant was collected and clarified by centrifugation prior to assay for presence of antibody.

Medium from transfected cells was assayed using a standard ELISA method for assembled IgG. This involved capture of the samples and standards onto a 96-well plate coated with an anti-human IgG Fc. Bound analyte was revealed with an anti-human kappa chain antibody linked to horseradish peroxidase and the chromogenic substrate tetra methylbenzidine. Color development was proportional to the amount of assembled antibody present in the sample. Standard samples were prepared from a commercially obtained stock of $IgG_4$/kappa antibody. The results showed that the DGV encoding the PG110 heavy and light chains was capable of expressing assembled antibody.

Example 2

Binding Characteristics of Mutated Anti-NGF Antibody PG110

In this example, the binding specificity and binding kinetics of PG110, the mutated anti-NGF antibody prepared as described in Example 1, was examined.

A. Binding Specificity

The selectivity profile of PG110 binding to human neurotrophins was determined using an Enzyme-Linked ImmunoSorbent Assay (ELISA) binding assay. ELISA plates were coated with 100 ng/well of either human NGF (R&D Systems, Cat. No. 256-GF), brain-derived neurotrophic factor (BDNF) (R&D Systems, Cat. No. 248-BD), neurotrophin 3 (NT3) (R&D Systems, Cat. No. 267-N3) or neurotrophin 4 (NT4) (R&D Systems, Cat. No. 268-N4). PG110 was added to neurotrophin-coated wells in the concentration range 3 pM-3 nM. After washing (PBS in 0.5% (v/v) Tween 20, pH 7.3), PG110 binding was detected using a biotinylated anti-human IgG antibody (Rockland Immunochemical Inc., Cat. No. 609-1602) coupled with streptavidin-linked alkaline phosphatase (Sigma Aldrich, Cat. No. S2890), followed by development of a color reaction by addition of 4-methylumbelliferyl phosphate (Sigma Aldrich, Cat. No. M3168). The reaction product was quantified using a fluorimeter (excitation at 360 nm; emission at 440 nm).

The results are summarized in the graph of FIG. 1. PG110 bound to human NGF-coated wells in a concentration-dependent manner, with a half-maximal binding concentration of 726 pM (derived from triplicate determinations on a single assay plate). In contrast, PG110 did not show measurable binding to assay wells coated with human BDNF, NT3, or NT4, which were otherwise detectable using positive control antibodies specific for these neurotrophins These results demonstrate that PG110, when tested at concentrations up to 3 nM in vitro, specifically binds to human NGF and displays no cross-reactivity to related neurotrophins.

B. Binding Kinetics

BIAcore analysis was used to evaluate the binding kinetics of the interaction between PG110 and either recombinant rat NGF (rrNGF) or recombinant human NGF (rhNGF).

Recombinant human beta nerve growth factor (rhNGF) (R&D Systems, Cat. No. 256 GF/CF) or recombinant rat beta nerve growth factor (rrNGF) (R&D Systems, Cat. No. 556 GF/CF) was immobilized covalently on CM5 sensor chips (GE Healthcare, formerly Biacore AB, Uppsala, Sweden) via primary amine groups using the amine coupling kit (GE Healthcare), with HBSEP (10 mM 4-(2-hydroxyethyl)-1-piperazineethanesulfonic acid (HEPES), 150 mM NaCl, 3 mM ethylene-diamine-tetraacetic acid (EDTA) and 0.005% Tween® 20, pH 7.4) as running buffer. The sensor chip surface was activated by injection of a mixture of 400 mM N-(3-Dimethylaminopropyl)-N'-ethylcarbodiimide (EDC) and 100 mM N-Hydroxysuccinimide (NHS) (1:1, v/v) for 7 minutes at a flow rate of 10 µl/min. 13-NGF (rh or rr) was diluted to 200 ng/ml in 10 mM sodium acetate pH 4.0 and the diluted solution was injected over the activated surface for various times to yield different surface densities. For quantitative interaction analyses, a surface density of 60 RU was prepared by injection of 50 µl diluted β-NGF (contact time 5 minutes). Non-reacted NHS esters were deactivated with 70 µl (contact time 7 minutes) ethanolamine solution (1 M, pH 8.5).

The parameters for the experiments performed with immobilized NGF were as follows: running buffer: HBSEP containing 100 µg/ml bovine serum albumin; flow rate: 25 µl/min; temperature: 37° C.; ligand density: 60 RU/60 RU (for rhNGF/rrNGF); analyte: PG110 concentrations: 2 nM, 4 nM, 8 nM, 17 nM, 33 nM, and 66 nM in running buffer; contact time: 240 seconds; dissociation time: 600 seconds; regeneration: 2×1 min. 10 mM glycine, pH 1.5.

Data and kinetic evaluations were done with GraphPad Prism software (version 5.01, GraphPad Software Inc., San Diego, Calif.) and BIAevaluation software (version 4.0.1, GE Healthcare), fitting data to the 1:1 Langmuir binding model.

The results are summarized below in Table 1 (wherein $K_{ass}$ indicates association rate constant, $K_{diss}$ indicates dissociation rate constant and $K_D$ indicates equilibrium dissociation constant). The data indicate mean±(sem) of 3 separate determinations

TABLE 1

Kinetic Constants of PG110 Interaction with Immobilized NGF

| Analyte | Ligand | $K_{ass}$ (l mol$^{-1}$s$^{-1}$) | $K_{diss}$ (s$^{-1}$) | $K_D$ |
|---|---|---|---|---|
| PG110 | rh NGF | $1.6 \times 10^5 \pm 3.5 \times 10^3$ | $1.2 \times 10^{-5} \pm 3.0 \times 10^{-6}$ | 72 ± 2 pM |
| PG110 | rr NGF | $1.7 \times 10^5 \pm 2.0 \times 10^3$ | $1.5 \times 10^{-5} \pm 5.6 \times 10^{-6}$ | 92 ± 34 pM |

The results of the study showed that PG110 interactions with NGF were characterized by high affinity binding and that no significant difference in the affinity ($K_D$) for either species homologue (human vs. rat) could be detected.

A further analysis of the binding kinetics was performed using PG110 Fab material generated by fragmentation of PG110 on Papain-Sepharose (Thermo Scientific). Immobilization of rhNGF was performed using HBSEP as running buffer at 25° C. Sensor chip surfaces were activated by injection of a mixture of 200 mM EDC and 50 mM NHS (1:1, v/v) for 7 minutes at a flow rate of 10 µl/min. rhNGF was diluted to 500 ng/ml in 10 mM sodium acetate pH 4.0 and 20 µl (contact time 2 minutes) of the diluted solution was injected over the activated surfaces of each of three cells to produce immobilization levels of 93.1, 100.3 and 88.7 RU. Non-reacted NHS esters were deactivated with 70 µl (contact time 7 minutes) ethanolamine (1 M, pH 8.5).

A series of concentrations of PG110 Fab (0.39, 0.78, 1.56, 3.13, 6.25, 12.5 and 25 nM), in 250 µl, were passed over freshly immobilized rhNGF surfaces at a flow rate of 50 µl/min, 37° C. in a running buffer of HPSEP containing 100

µg/ml bovine serum albumin. Dissociation was monitored for 30 minutes, and after interaction analysis complete regeneration was achieved with one pulse (30 µl) of 10 mM glycine pH 1.5. Additionally, to define the very slow $k_{diss}$ more precisely, the dissociation of one high concentration (100 nM) of PG110 Fab was monitored for 8 hours on each rhNGF surface and used for quantification of the dissociation rate constant ($k_{diss}$). The data were fit globally by a 1:1 Langmuir binding model using a fixed $k_{diss}$, determined from the extended dissociation measurement. To evaluate reproducibility of the kinetic constants analyses were performed in triplicate on the three freshly immobilized surfaces. The calculated kinetic constants are summarized in Table 2.

TABLE 2

Kinetic constants of PG110 Fab interaction with immobilized rhNGF.

| Analyte | Immobilisation Level | $K_{ass}$ (l mol$^{-1}$s$^{-1}$) | $K_{diss}$ (s$^{-1}$) | $K_D$ |
|---|---|---|---|---|
| PG110 Fab | 93.1 | $3.6 \times 10^5$ | $1.1 \times 10^{-5}$ | 31.3 pM |
| | 100.3 | $3.6 \times 10^5$ | $1.2 \times 10^{-5}$ | 32.7 pM |
| | 88.7 | $4.4 \times 10^5$ | $1.2 \times 10^{-5}$ | 27.8 pM |
| Mean | | $3.8 \times 10^5 \pm 0.5 \times 10^5$ | $1.1 \times 10^{-5} \pm 0.06 \times 10^{-5}$ | $30.6 \pm 0.25$ pM |

Example 3

Functional Characteristics of Mutated Anti-NGF Antibody PG110

In this example, various functional properties of PG110, the mutated anti-NGF antibody prepared as described in Example 1, were examined in in vitro assay.

A. Inhibition of NGF Binding to TrkA and p75$^{NTR}$ Receptors

Radioligand binding studies were conducted to compare the inhibitory effect of PG110 on binding of NGF to human TrkA and p75$^{NTR}$ receptors. HEK293 cells expressing either full-length human TrkA or p75$^{NTR}$ receptors were incubated with 2 nM $^{125}$I-NGF in the presence of PG110 at a final concentration of 0.01-100 nM. Unlabeled NGF (varying in concentration from 0-1 µM) also was included in the reactions. The reactions were performed in high-walled PT1276 flat-bottomed disposable tubes (Thermo Life Sciences). First, the radiolabeled NGF, unlabeled NGF and PG110 antibody were combined and incubated in the tubes for 10 minutes at room temperature, with shaking, in binding buffer (1×PBS, 0.9 mM CaCl, 0.5 mM MgCl, 0.1% BSA Fraction V, 0.1% (w/v) glucose). Then, 200 µl prepared cells (diluted to 5×10$^5$ cells/ml) were added. After a further 30 minutes incubation at room temperature with vigorous shaking, each reaction was divided across three plastic tubes (0.4 ml Microtube PE, Sarstedt 72.700), with 100 µl of the reaction being added to each tube. Each microtube already contained 200 µl of 150 mM sucrose in binding buffer. These tubes were then centrifuged at 20,000×g at 4° C. for 30 seconds to pellet the cells. The sucrose provides a density gradient which acts to sequester any displaced radiolabelled NGF. The tubes were then frozen in a dry ice/ethanol bath. The tips of these frozen tubes were then removed into separate plastic tubes (Naiad Ltd) for counting using a LKB Wallac mini-gamma counter to thereby quantify the $^{125}$I-NGF bound to the cells.

Figure 2A:
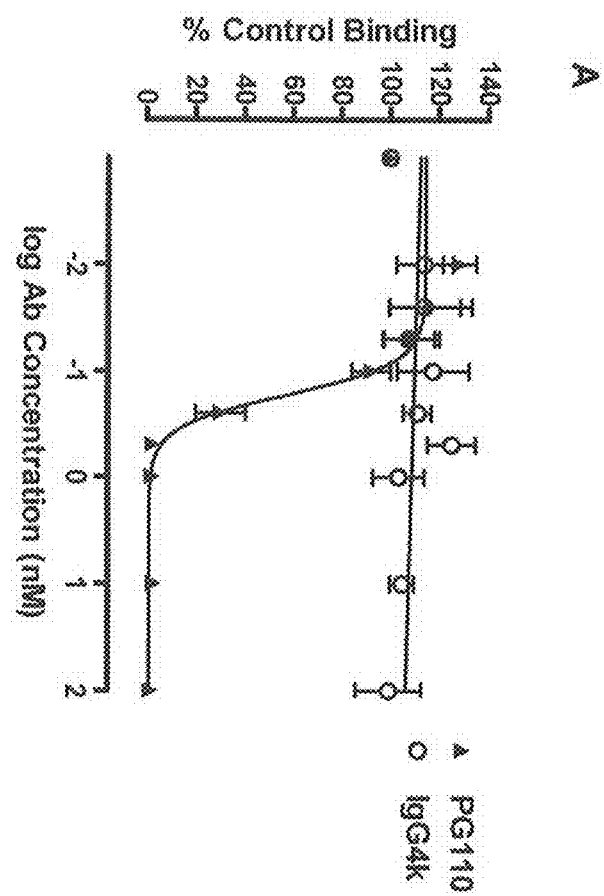
FIG. 2A is a graph showing inhibition of binding of NGF to the TrkA receptor by the PG110 antibody, as determined by a radiolabeled ligand binding experiment.
Figure 2B:
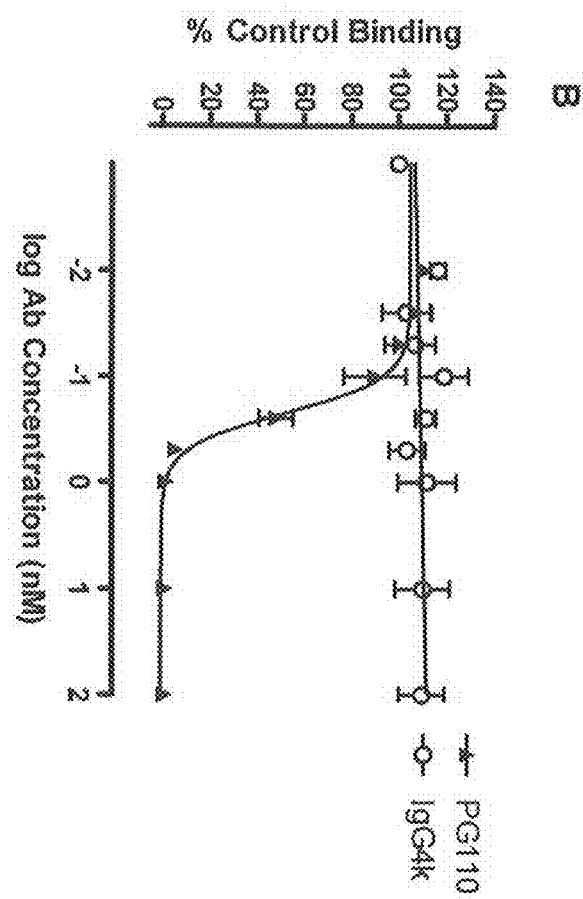
FIG. 2B is a graph showing inhibition of binding of NGF to the p75$^{NTR}$ receptor by the PG110 antibody, as determined by a radiolabeled ligand binding experiment.

The results are illustrated in the graphs of FIGS. 2A and 2B, in which the effect of PG110 on NGF binding to TrkA is shown in FIG. 2A and the effect of PG110 on NGF binding to p75$^{NTR}$ is shown in FIG. 2B. PG110 inhibited $^{125}$I-NGF binding to TrkA and p75$^{NTR}$ receptors in a concentration-dependent manner, with geometric mean (95% CI) IC$_{50}$ values of 170 (88-331) pM and 206 (86-491) pM, respectively (both n=3). An isotype control antibody did not inhibit $^{125}$I-NGF binding to either receptor. These results demonstrate that PG110 potently blocks the binding interaction of human NGF with both of its receptors in vitro.

B. TF-1 Cell Proliferation Assay

TF-1 is a human erythroleukaemic cell line that expresses human TrkA and proliferates in response to NGF. In these experiments, TF-1 cells were cultured in the presence of 10 ng/mL human, rat, or mouse recombinant NGF, with increasing concentrations of PG110 antibody, and cell proliferation was quantified 40 hours later using a colorimetric method based on the metabolic reduction of the yellow tetrazolium salt MTT [3-(4,5-dimethylthiazol-2-yl)-2,5-diphenyl tetrasodium bromide] to purple formazan.

Before use in the assay, TF-1 cells were cultured for 1 week in RPMI-1640 containing 10% fetal bovine serum (FBS) with 2 ng/ml GM-CSF (R&D Systems, Cat. No. 215-GM-50). Cells were washed, resuspended in RPMI-1640+10% FBS to a concentration of 300,000 cells/ml and replated on 96-well microplates (15,000 cells/well in 50 µl). At least 60 minutes after addition to the 96-well assay plates, cells were exposed to either human, rat or mouse recombinant NGF (10 ng/ml) in RPMI-1640 containing 10% FPB (50 µl/well) containing PG110 antibody. Medium containing NGF and test antibody was prepared at 2× final assay concentration at least 30 minutes before being added to pre-seeded cells. Test antibody was assayed in the concentration range of 0.6 ng/ml to 24 µg/ml. Control wells were included, either containing medium alone or containing TF-1 cells in the absence of NGF ("cellular blank"). Each treatment was performed in triplicate. After a 40 hour incubation period (37° C., 5% CO$_2$), proliferation was quantified using an MTT cell proliferation kit (ATCC Cat. No. 30-1010K). 10 µl MTT reagent was added before incubation for a further 4 hours at 37° C. Wells were then subsequently incubated with Detergent Reagent (100 µl/well; gentle mixing) for overnight incubation at room temperature in the dark. Thereafter, absorbance was recorded at 570 nm. Final average OD values for triplicate measurements were calculated by subtraction of the average value for the cellular blank.

Figure 3A:
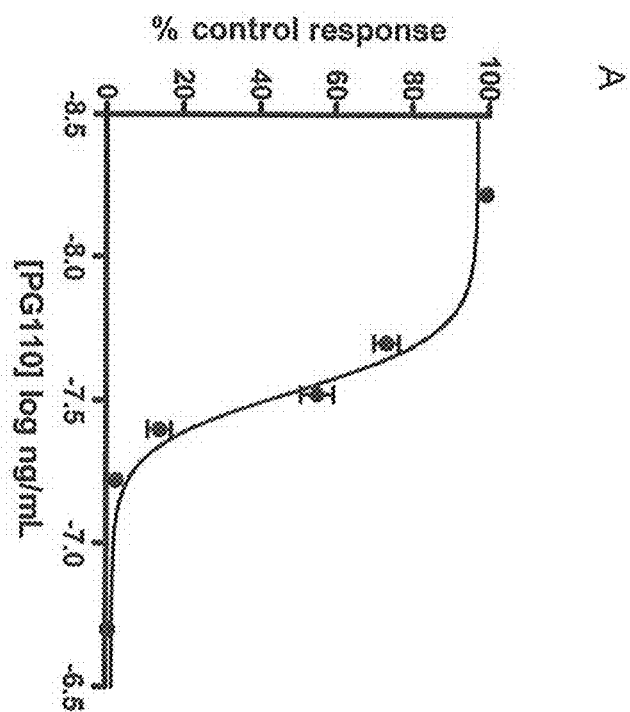
FIG. 3A is a graph showing the inhibitory effect of PG110 antibody on TF-1 cell proliferation stimulated by human NGF.
Figure 3B:
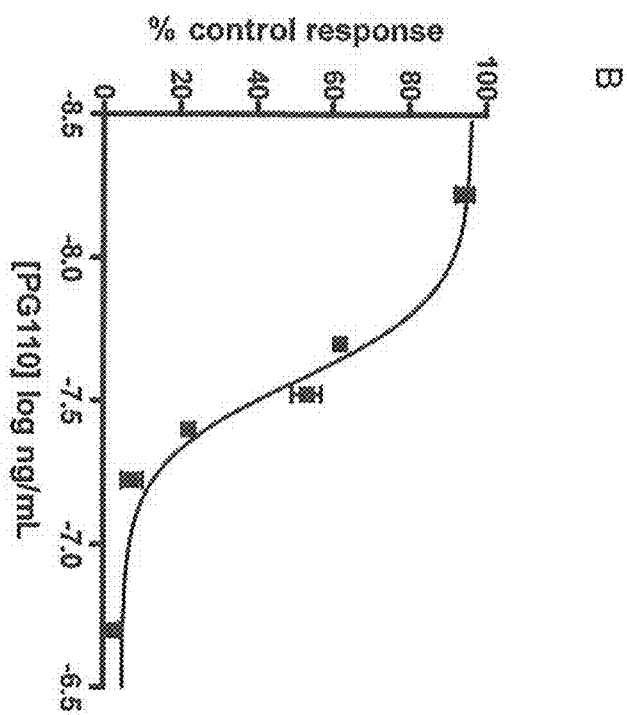
FIG. 3B is a graph showing the inhibitory effect of PG110 antibody on TF-1 cell proliferation stimulated by rat NGF.
Figure 3C:
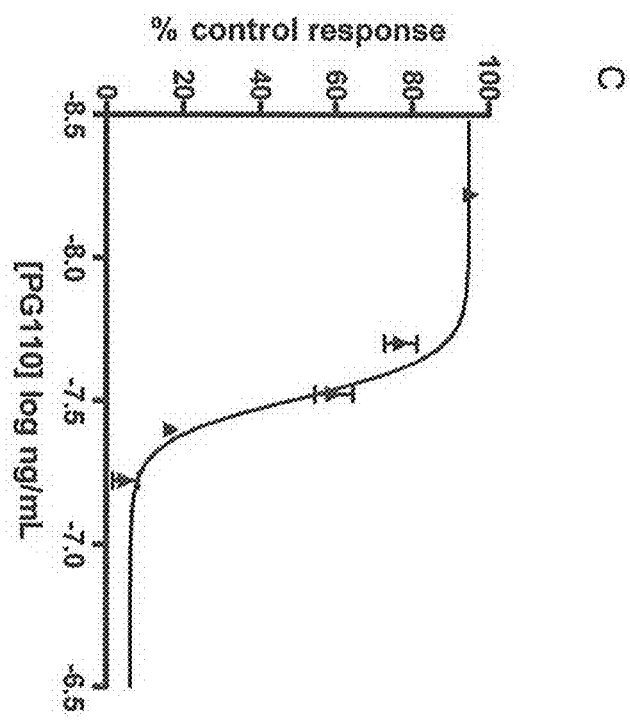
FIG. 3C is a graph showing the inhibitory effect of PG110 antibody on TF-1 cell proliferation stimulated by mouse NGF.

Incubation of TF-1 cells with NGF in the presence of PG110 (0.6 ng/mL-24 µg/mL) resulted in a concentration-related inhibition of cell proliferation. The results are illustrated in the graphs of FIGS. 3A-3C, wherein FIG. 3A shows the effect of PG110 treatment on TF-1 cell proliferation stimulated by human NGF, FIG. 3B shows the effect of PG110 treatment on TF-1 cell proliferation stimulated by rat NGF and FIG. 3C shows the effect of PG110 treatment on TF-1 cell proliferation stimulated by mouse NGF. PG110 demonstrated similar inhibitory potencies for all of the homologues of NGF tested and IC$_{50}$ values were approximately 30 ng/mL. The IC$_{50}$ values are summarized below in Table 3 (IC$_{50}$ values are expressed as ng/ml):

TABLE 3

Summary of $IC_{50}$ Values for PG110 in the TF-1 Cell Proliferation Assay

| Human Recombinant NGF | | | Rat Recombinant NGF | | | Mouse Recombinant NGF | | |
|---|---|---|---|---|---|---|---|---|
| Geomean | 95% CI | n | Geomean | 95% CI | n | Geomean | 95% CI | n |
| 29.4 | 26.5-32.7 | 5 | 27.8 | 24.5-31.6 | 5 | 30.8 | 27.4-34.5 | 3 |

The TF-1 cell proliferation assays demonstrate that PG110 equipotently neutralizes the activation of human TrkA receptors by human or rodent NGF.

C. Inhibition of Chick Dorsal Root Ganglion Survival

To test the ability of PG110 to inhibit the effect of NGF on sensory neurons, an in vitro assay using primary cultures of dorsal root ganglion (DRG) cells obtained from Day 8 chick embryos was used. Under these conditions, the survival of chick DRGs is dependent on the presence of exogenous NGF added to the culture medium.

Dorsal root ganglion were isolated from day 8 chick embryos and collected in a 50 ml Falcon tube (in 5 ml F-12 Ham's nutrient mixture+Glutamax I: GIBCO 31765-027). In each experiment, the total number of ganglia collected was about 400, which approximately corresponds to 20 embryos. Ganglia were subsequently trypsinized for 5 minutes at 37° C. (Trypsin-EDTA Euroclone, ECB3052D) and dissociated with a 10 ml syringe (20 G "yellow" needle) 4-5 times before being centrifuged for 3 minutes at 800 rpm.

After careful removal of trypsin-containing medium, cells were resuspended in 10 ml of fresh medium (F-12 Ham's nutrient mixture+Glutamax I), followed by a repeat of the dissociation procedure, and the medium volume was adjusted for a seeding concentration of 100,000-400,000 cells/ml. Cells were seeded in the absence of treatments in half the final volume containing 20% horse serum (Euroclone ECS0091L), using 24-multi-well plates (Falcon 353047) that had been coated with poly-L-lysine (100x=1 mg/ml solution of poly-L-lysine hydrobromide; Sigma P2636) dissolved in distilled water (30 minutes under UV, followed by 30 minutes drying under sterile hood).

While cells were adhering to plates (30 minutes in 5% $CO_2$ incubator, 37° C.), solutions of either NGF or NGF/anti-NGF antibody were prepared at 2x concentration in half the final volume and added well by well to reach the correct final concentration (i.e., final % of horse serum=10%; final concentration of NGF=5 ng/ml). Control wells were included, containing DRG cells in the absence of NGF. Each condition was tested in duplicate. After the addition of either NGF or NGF/anti-NGF mixtures, the plates were returned to the incubator (5% $CO_2$, 37° C.). The number of cells was scored 48 hours later, by counting all DRG cells observed along the vertical diameter of each well (Nikon TMS microscope, 10× magnification). Only DRG cells were included in the counts, which were easily identifiable according to their morphological characteristics, i.e., round, brilliant, light-refracting cells with long neurites.

The NGF neutralizing potency of the PG110 antibody tested in the concentration range of 10 ng/ml to 25 µg/ml for neutralization of either recombinant human NGF (rhNGF), recombinant rat NGF (rrNGF) or recombinant mouse NGF (rmNGF). In these experiments, 100% inhibition of survival was equivalent to the number of cells counted when cells were cultured without NGF, in the absence of anti-NGF antibody. Conversely, 0% inhibition was equivalent to the number of cells counted when cells were exposed to 5 ng/ml of the relevant NGF isoform, in the absence of anti-NGF antibody.

Incubation of cells in the presence of PG110 (10 ng/mL-25 µg/mL) resulted in a concentration-dependant reduction in cell survival, with an $IC_{50}$ between 10 and 50 ng/mL for all species of NGF homologues (n=1). These data demonstrate that PG110 inhibits the activity of NGF on sensory neurones.

D. Inhibition of PC12 Cell Neurite Outgrowth

PC12 is a rat phaeochromocytoma (chromaffin cell-derived tumor) cell line that expresses both rat TrkA and p75NTR receptors. When cultured on collagen-coated plates in the presence of NGF, PC12 cells differentiate into sympathetic-like neurones, becoming flat and extending outgrowths (neurites). Inhibition of NGF-mediated neurite outgrowth was employed as a semi-quantitative in vitro measure of the ability of PG110 to inhibit the interaction of NGF with the rat TrkA and p75NTR receptors.

PC12 cells (ECAAC 88022401) were primed (i.e., pre-exposed to NGF) by washing 100,000 cells with serum-free medium (RPMI-1640 with Glutamax I, Gibco-Invitrogen 61870-010) and replating on collagen-treated plastic culture flasks (Type I collagen, BD 35-4236, was employed as a 0.5 mg/ml working solution) in RPMI-1640 with Glutamax-I containing 10% FBS and recombinant rat NGF (R&D Systems, Cat. No. 556-NG-100) (100 ng/ml). Before seeding, cells were gently passed at least 5 times through a 21 G needle to disaggregate cell clumps. The medium containing NGF was removed and changed twice during the 1 week period of priming.

At the end of this period, primed PC 12 cells were washed with serum-free medium and trypsinized (Trypsin-EDTA Euroclone, ECB3052D) for 2-3 minutes in a humidified incubator (5% $CO_2$, 37° C.). Trypsin was blocked by addition of serum-containing medium and cells were centrifuged, washed with serum-free medium and resuspended in RPMI-1640 with Glutamax-I containing 10% FBS. Cells were gently passed at least 5 times through a 21 G needle to disaggregate cell clumps before being replated on collagen-treated Petri dishes at a density of 50,000 cells/ml. Three dishes per assay condition were prepared. For antibody testing, a 2× incubation mixture (recombinant rat NGF+anti-NGF) was prepared 1 hour before addition to pre-seeded cells. The final concentration of NGF was 20 ng/ml, while the anti-NGF antibody was tested at four dilutions: 20 µg/ml, 2 µg/ml, 200 ng/ml and 20 ng/ml.

NGF-induced neurite outgrowth was scored after 72 hours. At that time, medium was removed and cells were washed with calcium- and magnesium-free PBS (GIBCO, 10010) and fixed for 30 minutes with 4% formaldehyde in PBS. Microscope images (20× magnification) were acquired using a Nikon Eclipse TE2000-E microscope and Leica IM1000 Image Manager software Inhibition of neurite outgrowth was evaluated and scores (++; +/−; −−) were attributed based on the number of cells displaying a non-differentiated phenotype (=absence of clearly defined neurites).

Incubation of cells in the presence of PG110 (20 ng/mL-20 µg/mL) inhibited NGF-mediated neurite outgrowth, with total inhibition evident at 200 ng/mL, highlighting that PG110 is an effective inhibitor of the interaction between rat recombinant NGF and its native rat neurotrophin receptors.

Example 4

In Vivo Stability of Mutated Anti-NGF Antibody PG110

In this example, the terminal elimination half life ($T_{1/2}$) of the PG110 antibody was determined in vivo in rats and in cynomolgus monkeys.

A. Rat Studies

Sprague-Dawley rats were given a 10-minute intravenous (IV) infusion of PG110 antibody at a dosage of 3 mg/kg, 30 mg/kg or 100 mg/kg on Study Days 1 and 56. Toxicokinetic data evaluation was performed using mean serum concentration and time points from 6 animals/time point in each group. The nominal blood collection times were: pre-dose and 0.25, 1, 3, 6 and 24 hours post-dose on Study Day 1 and 56 and also at 48, 96, 168, 336, 504, 672, 840, 1008 and 1176 hours post-dose on Study Day 1. Serum sample bioanalysis was performed by Alta Analytical Laboratory using a validated ELISA method. Pharmacokinetic data analysis was performed using SNBL USA Pharmacokinetics Analysis System 2.0 with WinNonlin Professional version 4.0 software (Pharsight Corp.).

After IV administration, $T_{max}$ values (the time to maximal serum concentration) ranged from 0.25 to 1 hour, the first two sample collection time points. All animals displayed biphasic disposition with terminal elimination half-lives of approximately 8 to 9 days. More specifically, the $T_{1/2}$, in hours, for the three treatment groups is summarized below in Table 4:

TABLE 4

Terminal Elimination Half Life of PG110 in Sprague-Dawley Rats

| Dose Level (mg/kg) | Terminal Elimination Half-Life (hours) |
|---|---|
| 3 | 217 |
| 30 | 192 |
| 100 | 207 |

Thus, the group mean half-life values ranged from 192-217 hours (8-9 days) in the rats.

B. First Monkey Study

Cynomolgus monkeys were given a single, approximately 30-minute, intravenous (IV) infusion of PG110 antibody at a dosage of 3 mg/kg, 30 mg/kg or 100 mg/kg. Animals were divided into males and females; each dose was tested on 2 males and 2 females (except only 1 female was tested at 30 mg/kg). The nominal blood collection times for toxicokinetic data analysis were: immediately post-dose (within 2 minutes of the end of the infusion), 0.25, 1, 3, 6, 24, 48, 96, 168, 336, 504, 672, 840, 1008, 1176, 1344, 1512 and 1680 hours post end of the infusion. Serum sample bioanalysis was performed by Alta Analytical Laboratory using a validated ELISA method. Pharmacokinetic data analysis was performed using SNBL USA Pharmacokinetics Analysis System 2.0 with WinNonlin Professional version 4.0 software (Pharsight Corp.).

After IV administration, $T_{max}$ values (the time to maximal serum concentration) measured from the start of infusion ranged from the end of the infusion to approximately 1.6 hours. All animals displayed biphasic disposition (with the exception of the one female treated with 30 mg/kg, who showed an abrupt decline after the 504 hour timepoint) with terminal elimination half-lives of approximately 15-22 days. More specifically, the $T_{1/2}$, in hours, for the six treatment groups is summarized below in Table 5:

TABLE 5

Terminal Elimination Half Life of PG110 in Cynomolgus Monkeys

| Dose Level (mg/kg) | Sex | Terminal Elimination Half-Life (hours) |
|---|---|---|
| 3 | F (n = 2) | 370 |
|   | M (n = 2) | 531 |
| 30 | F (n = 1) | 471 |
|   | M (n = 2) | 450 |
| 100 | F (n = 2) | 383 |
|   | M (n = 2) | 461 |

Thus, the group mean half life values ranged from 370-531 hours (15-22 days) in the cynomolgus monkeys. Mean half life values generally were longer for males than for females, although given the small number of animals studied it is not clear whether this is a statistically significant difference.

C. Second Monkey Study

Cynomolgus monkeys were given weekly intravenous infusions of PG110 antibody over a period of four weeks. An approximately 30-minute, intravenous (IV) infusion of PG110 antibody, at a dosage of 3 mg/kg, 30 mg/kg or 100 mg/kg, was given on days 1, 8, 15 and 22. Animals were divided into males and females; each dose was tested on 3 males and 3 females. Serial blood samples were collected at the following nominal timepoints: pre-dose, immediately post-dose (within 2 minutes of the end of the infusion), 0.25, 1, 3, 6, 24 and 168 hours after infusion end on days 1 and 22. Additional samples were collected from all animals pre-dose on day 15 and from recovery animals at 336, 504, 672, 840, 1008, 1176, 1344, 1512, 1680, 1848, 2016 and 2208 hours following the final dose administration on day 22. Hours listed beginning at 24 hours after infusion correspond to pharmacokinetic days 1, 7, 14, 21, 28, 35, 42, 49, 56, 63, 70, 77, 84 and 92. All actual blood times were converted to begin from the start of the infusion.

Serum sample bioanalysis for PG110 concentration analysis was performed by Alta Analytical Laboratory using a validated ELISA method. Pharmacokinetic data analysis was performed using SNBL USA Pharmacokinetics Analysis System 2.0 with WinNonlin Professional version 4.0 software (Pharsight Corp.).

After IV administration, the group mean $T_{max}$ values (the time to maximal serum concentration) measured from the start of infusion ranged from approximately 0.6 hours to 2.6 hours. All animals displayed biphasic disposition, with terminal elimination half-lives of approximately 21-28 days (503 to 685 hours). More specifically, the $T_{1/2}$, in hours, for the six treatment groups is summarized below in Table 6:

TABLE 6

Terminal Elimination Half Life of PG110 in Cynomolgus Monkeys

| Dose Level (mg/kg) | Sex | Terminal Elimination Half-Life (hours) |
|---|---|---|
| 3 | F (n = 3) | 503 |
|   | M (n = 3) | 564 |
| 30 | F (n = 3) | 511 |
|   | M (n = 3) | 619 |
| 100 | F (n = 3) | 532* |
|   | M (n = 3) | 685 |

*based on n = 2 value

Thus, the group mean half life values ranged from approximately 21-28 days in the cynomolgus monkeys. Mean half life values generally were longer for males than for females, although given the small number of animals studied it is not clear whether this is a statistically significant difference.

Example 5

Potency of PG110 Compared to Rat Precursor Antibody

In this example, additional experiments were performed using the TF1 cell proliferation assay (as described in Example 3B, above) to compare the NGF-neutralizing potency of PG110 with its precursor, rat αD11. The rat αD11 antibody was supplied as two separate batches, one at a stock concentration of 0.73 mg/ml and the other at a stock concentration of 0.63 mg/ml. The PG110 and rat αD11 antibodies were evaluated in assays of TF1 cell proliferation mediated by human NGF or rat NGF, using the MTT cell proliferation kit (ATCC Cat. No. 30-1010K).

Before use in the assays, TF1 cells were cultured for one week in RPMI-1640 (ATCC cat. #30-2001) containing 10% fetal bovine serum (FBS, Cambrex DE14-801F, Lot 6SB0006) with 2 ng/ml GM-CSF (R&D Systems, cat. #215-GM-50). Cells were washed, resuspended in RPMI-640+ 10% FBS to a concentration of 300,000 cells/ml and replated on 96-well microplates (15,000 cells/well, in 50 μl).

At least 60 minutes after addition to 96-well assay plates, cells were exposed to either human or mouse recombinant NGF (10 ng/ml) in culture medium (10% FBS in RPMI-1640; 50 μl/well) containing anti-NGF antibody. Medium containing NGF and test antibody was prepared at 2× final assay concentration, at least 30 minutes before being added to pre-seeded cells. Test antibodies were assayed in the concentration range 0.6 ng/ml to 24 μg/ml. Control wells were always included, either containing medium alone, or containing TF1 cells in the absence of NGF ("cellular blank"). Each treatment was performed in triplicate. After a 40 hour incubation period (37° C., 5% $CO_2$), 10 μl of MTT reagent was added before incubation for a further 4 hours at 37° C. Wells were subsequently incubated with Detergent Reagent (100 μl/well; gentle mixing) for overnight incubation at room temperature in the dark. Thereafter, absorbance was recorded at 570 nm. Final average OD values for triplicate measurements were calculated by subtraction of the average values for the cellular blank. Maximal inhibition was set corresponding to the average OD value observed for cells cultured without NGF, in the absence of test antibody. Zero inhibition was set corresponding to the average OD value observed for cells exposed to 10 ng/ml NGF in the absence of test antibody.

The inhibitory potencies of NGF antibodies were quantified as $IC_{50}$ values (i.e., the concentration of antibody required to reduce the NGF-mediated proliferative response by 50%) using GraphPad Prism v5.01 software Inhibition curves were plotted individually in order to obtain discrete $IC_{50}$ values for each test antibody in each experiment. Measures of cell proliferation were normalized with respect to maximum OD values obtained within that assay, in the absence of added test antibody. Normalized responses were then plotted against test antibody concentration on a log scale, and $IC_{50}$ values were derived using the GraphPad Prism non-linear curve fitting function 'log(inhibitor) vs response-variable slope'.

The inhibitory effect of PG110 as compared to its precursor antibody rat αD11 is summarized below in Table 7.

TABLE 7

Summary of IC50 Values (ng/ml) in TF1 Cell Proliferation Assay

| Antibody | Human NGF | | | Rat NGF | | |
|---|---|---|---|---|---|---|
| | Geomean | 95% CI | n | Geomean | 95% CI | n |
| PG110 | 27.0 | 25.8-28.3 | 2 | 26.2 | 13.6-50.4 | 2 |
| Rat αD11 (Batch 1) | 63.7 | 35.7-114 | 3 | 44.8 | 31.4-64.1 | 3 |
| Rat αD11 (Batch 2) | 107 | — | 1 | 54.9 | — | 1 |

The results indicate that the PG110 antibody has approximately 2-fold higher potency in neutralizing NGF activity as compared to its precursor antibody rat αD11. Furthermore, the potency values obtained for rat αD11 batch 2 suggest that this batch may have a lower potency than the batch 1 material.

Example 6

Anti-NGF Antibody PG110 Does Not Exhibit a Rebound Effect in an Animal Model

In this example, a rat skin lesion model was used to examine the activity of the PG110 mAb. The rat skin lesion model was developed based on the observations that rats treated with anti-NGF antibody develop a pruritic response, with a dose-dependent increase in scratching being observed. The lesioning was not associated with reduction of innervation to the epidermis. Furthermore, the rats exhibited fast recovery after elimination of the antibody. This skin lesion activity has only been observed in rodents, who have a grooming behaviour. Although not intending to be limited by mechanism, it is hypothesized that in the anti-NGF-treated rats there is continued grooming due to an impaired feedback loop to stop the scratching response, which results in cutaneous injury. The skin lesions can then be given a quantitative score as a measure of the activity of the anti-NGF antibody in the rats.

In various clinical studies on the activity of anti-NGF antibodies (such as the humanized antibody RN-642, described further in U.S. Patent Publication No. 20040237124 and Abdiche, Y. N. et al. (2008) *Protein Sci.* 17:1326-1335), it has been reported that the effectiveness of the antibody diminishes for a period after a dosing (e.g., days 14-21 after dosing), followed by a recovery of activity of the antibody. There are reports of increased pain and/or increased adverse events (such as abnormal sensations, ranging from allodynia to tingling, prickling or pins & needles sensation) during this period after a dosing in which the antibody activity diminishes. This diminishing of antibody activity for a period of time after a dosing is referred to herein as a "rebound effect."

To evaluate the effect of PG110 antibody on grooming and scratching behaviours in conscious rats, male and female Sprague Dawley rats were treated with PG110 mAb (0.003, 0.01, 0.03, 0.3 or 3 mg/kg), administered as an i.v. bolus, or with a vehicle control. The rats received one weekly dose for four weeks. The evaluation criteria were: number of grooming and scratching episodes, body temperature, latency to paw licking, latency to jump (attempts to escape) and number and severity score of skin lesions over time.

The results indicated that no skin lesions were observed in rats administered with vehicle, whereas in the groups of rats administered with PG110, skin lesions were observed in all animals at all antibody dosages tested. Moreover, the number and severity of skin lesions increased over time and increased with increasing dosages of antibody. The number of scratching episodes also was increased in the antibody-treated animals, but antibody treatment did not have any effect on grooming behaviour, body temperature, latency to paw licking or latency to jump (attempts to escape).

Figure 4:
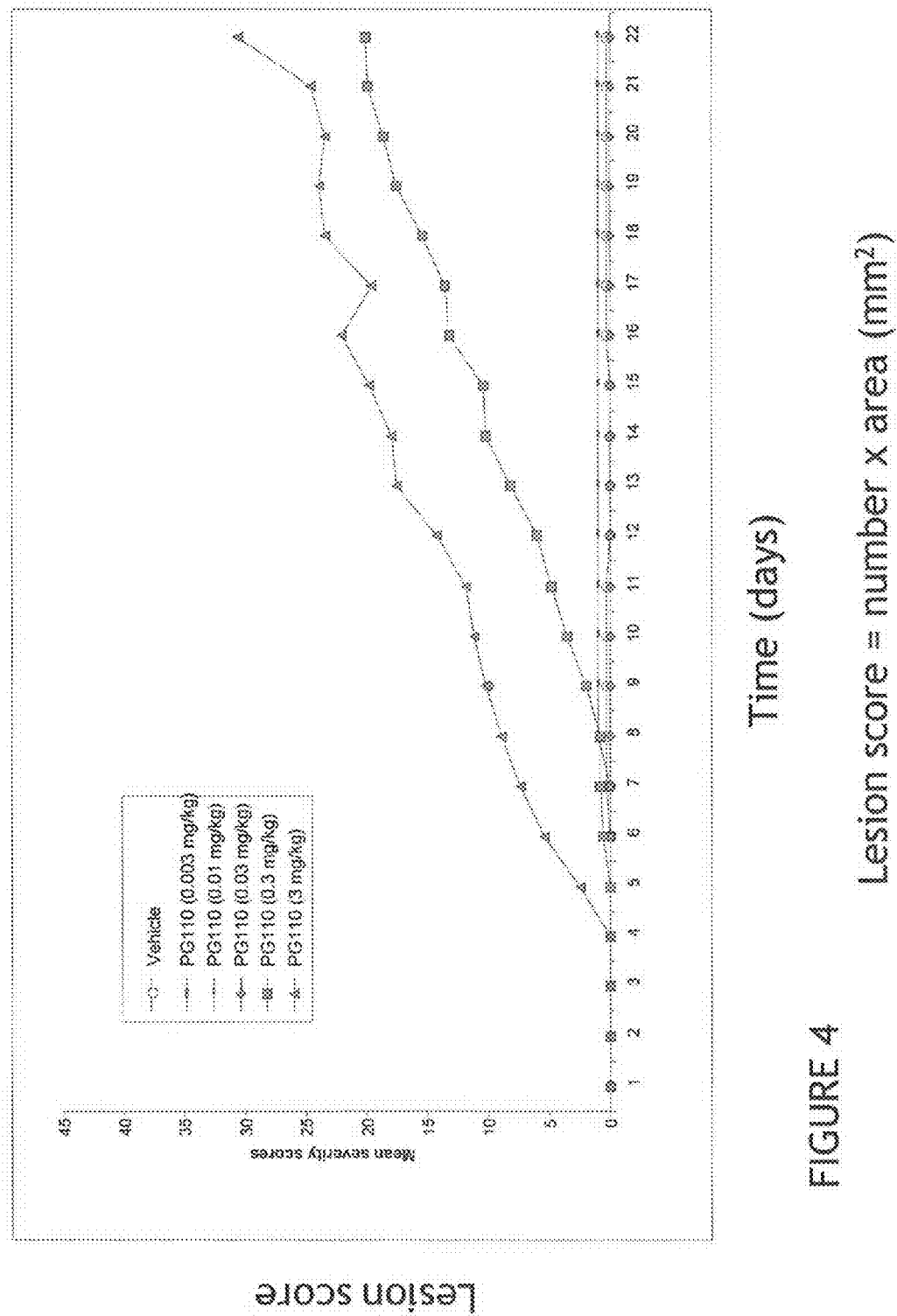
FIG. 4 is a graph showing the effect of PG110 antibody treatment on skin lesioning in rats.

The severity of the skin lesions was quantitated using a lesion score, which equals the number of lesions multiplied by the area (in mm$^2$) of the lesions. The lesion scores over time for PG110 treatment, compared to vehicle, are shown in the graph of FIG. 4. The results showed that the PG110-treated rats showed a steady increase in the lesion scores over time, in particular at the higher doses tested (0.3 mg/kg and 3 mg/kg). That is, the antibody did not exhibit a significant rebound effect over the course of the experiment, suggesting that it may be possible to select dosage and administration frequency parameters for use in humans such that a rebound effect can be avoided.

Thus, in summary, the rat skin lesion model illustrates an advantage of the PG110 anti-NGF antibody in that the PG110 antibody did not exhibit a noticeable rebound effect, which has been reported for other anti-NGF antibodies, suggesting that PG110 exhibits a more consistent and prolonged activity in vivo. Although not intended to be limited by mechanism, it is thought that this ability of PG110 to avoid a rebound effect in vivo is related to the prolonged terminal elimination half life observed for this antibody.

Example 7

PG110 Human Pharmacokinetics

PG110 is expected to have a half life in humans of about 10-30 days (range 10 to 40 days) with a multiphasic disposition. Based on a target $C_{min}$ value of ~0.25 μg/mL (range ~0.13 μg/mL to 0.40 μg/mL), human IV doses of 10 mg (~0.15 mg/kg; range ~0.1 mg/kg [5 mg] to ~0.2 mg/kg [15 mg]) every 4-12 weeks and SC doses of 20 mg (~0.3 mg/kg; range ~0.2 mg/kg [15 mg] to ~0.4 mg/kg [30 mg]) every 4-12 weeks are expected to be efficacious.

Human pharmacokinetics projections were based on the concentration data from two species (rat and monkey). Human pharmacokinetics were projected using multiple methods that included scaling of monkey and rat pharmacokinetic parameters, fixed allometric scaling, and methods based on preclinical and clinical data from other monoclonal antibodies. Projections were performed for both mono and biphasic disposition.

Method 1:

Human pharmacokinetic projections were based on 2-compartment model fitting PG110 concentration-time profiles in two species (rat and monkey). Human pharmacokinetic parameters of PG110 were projected using allometric scaling with fixed exponents of monkey and rat pharmacokinetic parameters.

For clearance:

$$CL_{human} = CL_{animal} \cdot \left(\frac{BW_{human}}{BW_{animal}}\right)^{0.67}$$

For volume of distribution:

$$V_{human} = V_{animal} \cdot \frac{BW_{human}}{BW_{animal}}$$

TABLE 8

Human Pharmacokinetic Parameters Predictions Based on Allometric Scaling with Fixed Exponents

| | $V_1$ mL/kg | CL mL/hr/kg | $V_2$ mL/kg | $CL_D$ mL/hr/kg |
|---|---|---|---|---|
| | Model-Fitted Pharmacokinetic Parameters | | | |
| Rat | 40.2 | 0.22 | 36.5 | 2.23 |
| Monkey | 29.3 | 0.10 | 31.1 | 1.78 |
| | Predicted Human Pharmacokinetic Parameters | | | |
| Predicted Human Value Based on Rat | 40.2 | 0.034 | 36.5 | 0.35 |
| Predicted Human Value Based on Monkey | 29.3 | 0.042 | 31.1 | 0.75 |
| Average | 34.7 | 0.038 | 33.8 | 0.55 |

PG110 human half-life is then calculated based on the predicted human CL and $V_1$. The predicted PG110 human half-life was 26 days.

Method 2:

Human pharmacokinetic projections were based on the observed data from two species (rat and monkey). Human CL and V were projected using the same method as in Method 1. Human half-life for PG110 was projected using modified allometric scaling with fixed exponent at 0.25:

$$T_{1/2,human} = T_{1/2,animal} \cdot \left(\frac{BW_{human}}{BW_{animal}}\right)^{0.25}$$

TABLE 9

Human Pharmacokinetic Parameters Predictions Based on Modified Allometric Scaling with Fixed Exponent

| | CL (mL/hr/kg) | | $V_{ss}$ (mL/kg) | | $t_{1/2}$ (days) | |
|---|---|---|---|---|---|---|
| | Rat | Monkey | Rat | Monkey | Rat | Monkey |
| PG110 Observed | 0.22 | 0.098 | 70 | 60 | 8.6 | 19.1 |
| Predicted Human Values | 0.0343 | 0.0410 | 70 | 60 | 35.2 | 37 |
| Predicted Human Values (Average) | 0.0376 | | 65 | | 36 | |

Using Method 2, the predicted PG110 human half-life was 36 days.

Method 3:

Human pharmacokinetic projections were based on PG110 data in rat and monkey and the preclinical and clinical pharmacokinetic parameters from other monoclonal antibodies. Scaling was based on observed PG110 half life in rats and monkeys and on the rat/human and monkey/human ratio of half life of other monoclonal antibodies. Estimated pharmacokinetic parameters (clearance, volume of distribution and half-life) of other monoclonal antibodies in rat and monkey were first compared to those in clinical studies. The differences between rat, monkey and human were estimated as a ratio of rat/human and monkey/human. Human pharmacokinetic parameters for PG110 were then estimated based on its pharmacokinetic parameters in rat or monkey with a correction of rat/human or monkey/human ratio for other monoclonal antibodies. Using Method 3, the predicted PG110 human half-life was 11-29 days.

TABLE 10

Human Pharmacokinetic Parameters Predictions Based on Past Experience with Other Monoclonal Antibodies

|  | CL (mL/hr/kg) | | $V_{ss}$ (mL/kg) | | $t_{1/2}$ (days) | |
| --- | --- | --- | --- | --- | --- | --- |
|  | R/H | M/H | R/H | M/H | R/H | M/H |
| Antibody 1 | 1.35 | 1.88 | 1.33 | 0.53 | 0.93 | 0.69 |
| Antibody 2 | 3.57 | 1.43 | 1.65 | 0.72 | 0.44 | 0.49 |
| Antibody 3 | 1.58 | 1.46 | 1.35 | 0.71 | 1.05 | 0.78 |
| Average | 2.17 | 1.59 | 1.45 | 0.65 | 0.81 | 0.65 |
|  | Rat | Monkey | Rat | Monkey | Rat | Monkey |
| PG110 Observed | 0.22 | 0.098 | 70 | 60 | 8.6 | 19.1 |
| Predicted Human Values | 0.101 | 0.062 | 48.4 | 92.0 | 11 | 29 |

R/H: rat/human,
M/H: monkey/human

Method 4:

Human pharmacokinetic projections were based on 2-compartment model fitting PG110 concentration-time profiles in two species (rat and monkey). Human pharmacokinetic parameters of PG110 were projected using allometric scaling with regression of monkey and rat pharmacokinetic parameters.

For both clearance and volume of distribution:

$$\text{Log(Pharmacokinetic Parameter)} = a \times \text{Log(BW)} + b$$

A linear regression was conducted based on rat and monkey pharmacokinetic parameters and body weight (BW) to estimate the slope (a) and intercept (b). Human pharmacokinetic parameters of PG110 were then estimated using typical human BW and the estimated slope and intercept.

TABLE 11

Human Pharmacokinetic Parameters Predictions Based on Allometric Scaling with Regression

|  | BW kg | LnBW kg | V1 mL | CL mL/hr | V2 mL | $CL_D$ mL/hr |
| --- | --- | --- | --- | --- | --- | --- |
| Rat | 0.25 | -1.387 | 2.307 | -2.907 | 2.210 | -0.585 |
| monkey | 5 | 1.609 | 4.988 | -0.680 | 5.047 | 2.188 |

TABLE 11-continued

Human Pharmacokinetic Parameters Predictions Based on Allometric Scaling with Regression

|  | BW kg | LnBW kg | V1 mL | CL mL/hr | V2 mL | $CL_D$ mL/hr |
| --- | --- | --- | --- | --- | --- | --- |
| | | | Estimated slope and Intercept Based on Linear Regression1 | | | |
| Slope | | | 0.8949 | 0.7432 | 0.947 | 0.9255 |
| Intercept | | | 3.5475 | -1.8766 | 3.523 | 0.6982 |
| | | | Predicted Human Pharmacokinetic Parameters | | | |
| Human | 70 | 4.248 | 1555 | 3.600 | 1894 | 103 |

PG110 human half-life is then calculated based on the predicted human pharmacokinetic parameters. The predicted PG110 human half-life was 12 days.

Based on these methods, PG110 is expected to have a half life in humans of about 15-30 days (range 10 to 40 days) with a biphasic disposition (predicted pharmacokinetic parameters: $V_1$=2.5 L, CL=5.0 mL/hr, $V_2$=2.5 L, $CL_D$=40 mL/hr).

Example 8

Treatment of Osteoarthritis in Humans with PG110

A human clinical study was initiated to test the safety, tolerability, and pharmacokinetics of PG110 in patients with pain attributed to osteoarthritis of the knee. The design of the study and preliminary results are described below.

In this Phase I, single centre, placebo-controlled, double-blind, single ascending dose study, six (6) dose levels were evaluated: 0.003, 0.01, 0.03, 0.1, 0.3 and 1 mg/kg. Per dose level, a cohort of 7 patients with pain attributed to osteoarthritis of the knee (42 patients in total) were randomly assigned in a 6:1 ratio to active or placebo treatment. Each patient was administered a single dose of PG110 or placebo intravenously over 2 h interval on the morning of Day 0 after a light breakfast. Patients remained at the Clinical Pharmacology Unit (CPU) until approximately 24 h after start of infusion (Day 1) and returned for visits on Days 4, 7, 14, 21, 28, 56 and 84 of the study.

Blood samples for PG110 assay were taken on Day 0 (pre-dose, 1, 2, 3, 6 and 12 hours) and on Days 1, 4, 7, 14, 21, 28, 56 and 84 post-dose. Serum concentrations of PG110 were determined using a validated ELISA assay. Anti-PG110 assays were also performed on Days 0 (pre-dose), 14, 28, 56 and 84 samples.

Pharmacodynamic assessments, including patient assessment of pain, Western Ontario and McMaster Universities (WOMAC™) Osteoarthritis Index questionnaire, McGill pain questionnaire, 6-Minute Walk Test, Ultrasound of the knee and hs-CRP, were conducted in the study.

Preliminary results for patient assessment of pain are summarized in Table 12. A patient assessment of pain was used as an assessment of pain intensity. The patients were asked to score their answer on a 0-100 mm VAS where 0 mm equals no pain and 100 mm equals worst pain.

TABLE 12

PG110 in OA Patients: Patient Assessment of Pain (VAS)

| Time | Patient Assessment of Pain (VAS, mm, Change from Baseline) (Mean ± SD) | | | | | |
| --- | --- | --- | --- | --- | --- | --- |
| (Day) | Placebo | 0.003 mg/kg | 0.01 mg/kg | 0.03 mg/kg | 0.1 mg/kg | 0.3 mg/kg |
| 4 | -7.2 ± 13.1 | -15.8 ± 23.0 | -22.8 ± 28.6 | -16.5 ± 17.5 | -23.0 ± 17.6 | -31.7 ± 18.2 |
| 7 | -10.2 ± 12.1 | -14.8 ± 23.4 | -12.3 ± 25.9 | -26.0 ± 17.2 | -34.8 ± 20.3 | -32.5 ± 18.2 |
| 14 | -10.6 ± 14.3 | -29.7 ± 15.8 | -12.5 ± 21.7 | -15.5 ± 22.7 | -24.3 ± 28.3 | 0.5 ± 17.2 |

TABLE 12-continued

PG110 in OA Patients: Patient Assessment of Pain (VAS)

Patient Assessment of Pain (VAS, mm, Change from Baseline) (Mean ± SD)

| Time (Day) | Placebo | 0.003 mg/kg | 0.01 mg/kg | 0.03 mg/kg | 0.1 mg/kg | 0.3 mg/kg |
|---|---|---|---|---|---|---|
| 21 | −11.2 ± 24.1 | −30.5 ± 23.9 | −16.3 ± 24.9 | −25.5 ± 24.1 | −23.3 ± 40.7 | −20.0 ± 18.5 |
| 28 | −9.6 ± 11.9 | −28.3 ± 25.9 | −16.5 ± 22.8 | −30.7 ± 22.5 | −45.2 ± 22.4 | −35.3 ± 20.5 |
| 56 | 0.5 ± 15.0 | −24.3 ± 25.8 | −11.8 ± 19.8 | −24.0 ± 19.8 | −48.8 ± 23.7 | −52.8 ± 19.3 |
| 84 | −7.8 ± 16.4 | −25.0 ± 20.7 | −9.2 ± 18.2 | −21.0 ± 23.2 | −29.3 ± 37.1 | −34.0 ± 26.0 |
| Maximum Patient Assessment of Pain (VAS, mm) | −22.4 ± 13.0 | −41.0 ± 14.5 | −30.2 ± 25.3 | −37.2 ± 17.7 | −48.8 ± 23.7 | −55.3 ± 13.7 |

Based on the preliminary pharmacodynamic data, an apparent dose-response was observed in the 0 to 0.3 mg/kg PG110 dose range.

The pharmacologic half-life was estimated based on the average amount of time to maintain drug effect (MRT for drug effect). It is calculated as the ratio of area of the first moment baseline-corrected effect-time curve (AUMEC) vs. accumulated baseline-corrected drug effect over time (area under the effect-time curve, AUEC):

$$\text{Pharmacologic Half-life} = \frac{AUMEC}{AUEC} = \frac{\int E(t)t\,dt}{\int E(t)\,dt}$$

The estimated pharmacologic half-lives are summarized in Table 13.

TABLE 13

Pharmacologic Half-life for PG110

| | PG110 Dose | | | | |
|---|---|---|---|---|---|
| | 0.003 mg/kg | 0.01 mg/kg | 0.03 mg/kg | 0.1 mg/kg | 0.3 mg/kg |
| Pharmacologic Half-life (Mean ± SD) (Day) | 43.0 ± 7.5 | 30.9 ± 21.6 | 35.8 ± 17.9 | 42.7 ± 5.0 | 41.9 ± 5.4 |

Estimation of the pharmacologic half-life was based on data collected up to 84 days post PG110 dose. As there was still sustained effect of PG110 at Day 84, especially at 0.1 mg/kg and 0.3 mg/kg dose, the estimated mean pharmacologic half-life for PG110 is at least 5-7 weeks, with a range of at least 4-8 weeks.

The preliminary pharmacodynamic data are consistent with the projected therapeutic dose (0.10 to 0.3 mg/kg or 7-21 mg). The preliminary pharmacologic half-life suggests that every 4-12 week dosing may be effective.

EQUIVALENTS

Those skilled in the art will recognize, or be able to ascertain using no more than routine experimentation, many equivalents of the specific embodiments of the invention described herein. Such equivalents are intended to be encompassed by the following claims. Any combination of the embodiments disclosed in the dependent claims are contemplated to be within the scope of the invention.

INCORPORATION BY REFERENCE

All publications, patents, and pending patent applications referred to herein are hereby incorporated by reference in their entirety.

We claim:

1. An anti-nerve growth factor (NGF) antibody comprising (i) a heavy chain variable region comprising CDRs 1, 2 and 3 comprising the amino acid sequences of SEQ ID NOs: 3, 4 and 5, respectively, (ii) a light chain variable region comprising CDRs 1, 2 and 3 comprising the amino acid sequences of SEQ ID NOs: 6, 7 and 8, respectively, and (iii) a human IgG4 constant region, wherein the human IgG4 constant region comprises the amino acid sequence of SEQ ID NO: 10.

2. An anti-nerve growth factor (NGF) antibody comprising (i) a heavy chain variable region comprising the amino acid sequence of SEQ ID NO:1, (ii) a light chain variable region comprising the amino acid sequence of SEQ ID NO: 2, and (iii) a human IgG4 constant region, wherein the human IgG4 constant region comprises the amino acid sequence of SEQ ID NO: 10.

3. The anti-NGF antibody claim 1, which comprises a heavy chain variable region comprising the amino acid sequence of SEQ ID NO: 1.

4. The anti-NGF antibody claim 1, which comprises a light chain variable region comprising the amino acid sequence of SEQ ID NO: 2.

5. The anti-NGF antibody claim 1, which is a chimeric, humanized or human antibody.

6. A pharmaceutical composition comprising the anti-NGF antibody of claim 1 and a pharmaceutically acceptable carrier.

7. A kit comprising the anti-NGF antibody of claim 1 and instructions for use of the antibody in treating NGF-related pain.

8. An anti-nerve growth factor (NGF) antibody comprising a human IgG4 constant region, wherein the antibody comprises a heavy chain comprising the amino acid sequence of SEQ ID NO: 13 and comprises a light chain comprising the amino acid sequence of SEQ ID NO: 16.

9. An anti-nerve growth factor (NGF) antibody comprising a human IgG4 constant region, wherein the antibody comprises a heavy chain encoded by the nucleotide sequence of SEQ ID NO: 11, and a light chain encoded by the nucleotide sequence of SEQ ID NO: 14.

* * * * *

SEQUENCE LISTING

<160> NUMBER OF SEQ ID NOS: 16

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Asn
            20                  25                  30

Asn Val Asn Trp Val Arg Gln Ala Pro Gly Lys Gly Leu Glu Trp Val
        35                  40                  45

Gly Gly Val Trp Ala Gly Gly Ala Thr Asp Tyr Asn Ser Ala Leu Lys
    50                  55                  60

Ser Arg Phe Thr Ile Ser Arg Asp Asn Ser Lys Asn Thr Ala Tyr Leu
65                  70                  75                  80

Gln Met Asn Ser Leu Arg Ala Glu Asp Thr Ala Val Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Thr Asp Thr Leu His Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln His Tyr Phe His Tyr Pro Arg
                85                  90                  95

Thr Phe Gly Gln Gly Thr Lys Val Glu Ile Lys
            100                 105

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 3

Gly Phe Ser Leu Thr Asn Asn Asn Val Asn
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Val Trp Ala Gly Gly Ala Thr Asp Tyr Asn Ser Ala Leu Lys Ser
1               5                   10                  15

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Gly Gly Tyr Ser Ser Ser Thr Leu Tyr Ala Met Asp Ala
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Glu Asp Ile Tyr Asn Ala Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Thr Asp Thr Leu His Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln His Tyr Phe His Tyr Pro Arg Thr
1               5

<210> SEQ ID NO 9
<211> LENGTH: 327
<212> TYPE: PRT
<213> ORGANISM: Homo sapiens
```

<400> SEQUENCE: 9

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 10
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 10

```
Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
         20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 11
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atggaatgga gctgggtgtt cctgttcttc ctgagcgtga ccaccggcgt gcacagcgag    60
gtgcagctgg tcgagagcgg cggagggctg gtgcagccag cggcagcct gaggctgtcc   120 tgcgccgcca gcggcttcag cctgaccaac aacaacgtga actgggtgcg gcaggcccca   180
ggcaagggcc tggaatgggt gggcggcgtg tgggccgggg agccaccga ctacaacagc   240 gccctgaaga gcaggttcac catcagcagg gacaacagca gaacaccgc ctacctgcag   300
```

```
atgaacagcc tgagggccga ggacaccgcc gtgtactact gcgccaggga cggcggctac    360
agcagcagca ccctgtacgc catggacgcc tggggccagg gcaccctggt gaccgtgagc    420
agcgccagca ccaagggccc cagcgtgttc cccctggccc cctgcagcag aagcaccagc    480
gagagcacag ccgccctggg ctgcctggtg aaggactact cccccgagcc cgtgaccgtg    540
tcctggaaca gcggagccct gaccagcggg gtgcacacct tccccgccgt gctgcagagc    600
agcggcctgt acagcctgag cagcgtggtg acagtgccca gcagcagcct gggcaccaag    660
acctacacct gcaacgtgga ccacaagccc agcaacacca aggtggacaa gagggtggag    720
agcaagtacg gcccaccctg cccccccatgc ccagcccccg agttcctggg cggaccctcc    780
gtgtttctgt tccccccccaa gcccaaggac accctgatga tcagcaggac ccccgaggtg    840
acctgcgtgg tggtggacgt gagccaggaa gatccagagg tccagttcaa ctggtacgtg    900
gacggcgtgg aggtgcacaa cgccaagacc aagcccagag aggaacagtt taacagcacc    960
tacagggtgg tgtccgtgct gaccgtgctg caccaggact ggctgaacgg caaggagtac   1020
aagtgcaagg tctccaacaa gggcctgccc agctccatcg agaaaaccat cagcaaggcc   1080
aagggccagc cacgggagcc ccaggtgtac accctgccac cctcccagga gagatgacc    1140 aagaaccagg tgtccctgac ctgtctggtg aagggcttct accccagcga catcgccgtg   1200
gagtgggaga gcaacggcca gcccgagaac aactacaaga ccaccccccc agtgctggac   1260
agcgacggca gcttcttcct gtacagcagg ctgaccgtgg acaagtccag gtggcaggaa   1320
ggcaacgtct ttagctgcag cgtgatgcac gaggccctgc acaaccacta cacccagaag   1380
agcctgtccc tgagcctggg caagtga                                       1407
```

<210> SEQ ID NO 12
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Leu
        35                  40                  45

Thr Asn Asn Asn Val Asn Trp Val Arg Gln Ala Pro Gly Lys Gly Leu
    50                  55                  60

Glu Trp Val Gly Gly Val Trp Ala Gly Gly Ala Thr Asp Tyr Asn Ser
65                  70                  75                  80

Ala Leu Lys Ser Arg Phe Thr Ile Ser Arg Asp Asn Ser Lys Asn Thr
                85                  90                  95

Ala Tyr Leu Gln Met Asn Ser Leu Arg Ala Glu Asp Thr Ala Val Tyr
            100                 105                 110

Tyr Cys Ala Arg Asp Gly Gly Tyr Ser Ser Ser Thr Leu Tyr Ala Met
        115                 120                 125

Asp Ala Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

```
Glu Ser Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
        195                 200                 205
Val Val Thr Val Pro Ser Ser Ser Leu Gly Thr Lys Thr Tyr Thr Cys
    210                 215                 220
Asn Val Asp His Lys Pro Ser Asn Thr Lys Val Asp Lys Arg Val Glu
225                 230                 235                 240
Ser Lys Tyr Gly Pro Pro Cys Pro Pro Cys Pro Ala Pro Glu Phe Leu
                245                 250                 255
Gly Gly Pro Ser Val Phe Leu Phe Pro Pro Lys Pro Lys Asp Thr Leu
            260                 265                 270
Met Ile Ser Arg Thr Pro Glu Val Thr Cys Val Val Val Asp Val Ser
        275                 280                 285
Gln Glu Asp Pro Glu Val Gln Phe Asn Trp Tyr Val Asp Gly Val Glu
    290                 295                 300
Val His Asn Ala Lys Thr Lys Pro Arg Glu Glu Gln Phe Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Gly Leu Pro Ser Ser
            340                 345                 350
Ile Glu Lys Thr Ile Ser Lys Ala Lys Gly Gln Pro Arg Glu Pro Gln
        355                 360                 365
Val Tyr Thr Leu Pro Pro Ser Gln Glu Glu Met Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Arg Leu Thr
            420                 425                 430
Val Asp Lys Ser Arg Trp Gln Glu Gly Asn Val Phe Ser Cys Ser Val
        435                 440                 445
Met His Glu Ala Leu His Asn His Tyr Thr Gln Lys Ser Leu Ser Leu
    450                 455                 460
Ser Leu Gly Lys
465

<210> SEQ ID NO 13
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Ser Leu Thr Asn Asn
            20                  25                  30
Asn Val Asn Trp Val Arg Gln Ala Pro Gly Lys Gly Leu Glu Trp Val
        35                  40                  45
```

Gly Gly Val Trp Ala Gly Ala Thr Asp Tyr Asn Ser Ala Leu Lys
 50                  55                  60

Ser Arg Phe Thr Ile Ser Arg Asp Asn Ser Lys Asn Thr Ala Tyr Leu
 65                  70                  75                  80

Gln Met Asn Ser Leu Arg Ala Glu Asp Thr Ala Val Tyr Tyr Cys Ala
                 85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 14
<211> LENGTH: 705

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
atgagcgtgc ccacccaggt gctgggcctg ctgctgctgt ggctgaccga cgccagatgc      60
gacatccaga tgacccagag ccccagcagc ctgagcgcca cgtgggcga cagggtgacc     120
atcacctgca gggccagcga ggacatctac aacgccctgg cctggtatca gcagaagccc     180
ggcaaggccc ccaagctgct gatctacaac accgacaccc tgcacaccgg cgtgcccagc     240
aggttcagcg gcagcggctc cggcaccgac tacaccctga ccatcagcag cctgcagccc     300
gaggacttcg ccacctactt ttgccagcac tacttccact accccaggac cttcggccag     360
ggcaccaagg tggagatcaa gaggaccgtg gctgccccca gcgtgttcat cttcccccc      420
agcgacgagc agctgaagag cggcaccgcc tccgtggtgt gcctgctgaa caacttctac     480
ccccgggagg ccaaggtgca gtggaaggtg gacaacgccc tgcagagcgg caacagccag     540
gaaagcgtca ccgagcagga cagcaaggac tccacctaca gcctgagcag caccctgacc     600
ctgagcaagg ccgactacga aagcacaag gtgtacgcct gcgaggtgac ccaccagggc     660
ctgtccagcc ccgtgaccaa gagcttcaac aggggcgagt gctga                    705
```

<210> SEQ ID NO 15
<211> LENGTH: 234
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Met Ser Val Pro Thr Gln Val Leu Gly Leu Leu Leu Leu Trp Leu Thr
  1               5                  10                  15

Asp Ala Arg Cys Asp Ile Gln Met Thr Gln Ser Pro Ser Ser Leu Ser
             20                  25                  30

Ala Ser Val Gly Asp Arg Val Thr Ile Thr Cys Arg Ala Ser Glu Asp
         35                  40                  45

Ile Tyr Asn Ala Leu Ala Trp Tyr Gln Gln Lys Pro Gly Lys Ala Pro
     50                  55                  60

Lys Leu Leu Ile Tyr Asn Thr Asp Thr Leu His Thr Gly Val Pro Ser
 65                  70                  75                  80

Arg Phe Ser Gly Ser Gly Ser Gly Thr Asp Tyr Thr Leu Thr Ile Ser
                 85                  90                  95

Ser Leu Gln Pro Glu Asp Phe Ala Thr Tyr Phe Cys Gln His Tyr Phe
            100                 105                 110

His Tyr Pro Arg Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
```

His Lys Val Tyr Ala Cys Glu Val Thr His Gln Gly Leu Ser Ser Pro
            195                 200                 205
His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 16
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Thr Asp Thr Leu His Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln His Tyr Phe His Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210